United States Patent
LaBorde

(10) Patent No.: US 10,388,410 B1
(45) Date of Patent: Aug. 20, 2019

(54) SYSTEM, SERVER AND METHOD FOR PREVENTING SUICIDE

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 0 days.

(21) Appl. No.: 16/029,629

(22) Filed: Jul. 8, 2018

Related U.S. Application Data

(63) Continuation of application No. 15/950,060, filed on Apr. 10, 2018, now Pat. No. 10,043,591, which is a continuation-in-part of application No. 15/891,114, filed on Feb. 7, 2018, now Pat. No. 10,014,076, which is a continuation-in-part of application No. 15/704,494, filed on Sep. 14, 2017, now Pat. No. 9,928,342, which is a continuation-in-part of application No. 15/592,116, filed on May 10, 2017, now Pat. No. 9,848,827, which is a continuation of application No. 15/390,695, filed on Dec. 26, 2016, (Continued)

(51) Int. Cl.
G06K 7/10 (2006.01)
G06N 3/04 (2006.01)
G06N 3/08 (2006.01)
G16H 10/65 (2018.01)
G16H 50/30 (2018.01)

(52) U.S. Cl.
CPC .......... *G16H 10/65* (2018.01); *G06K 7/10366* (2013.01); *G06N 3/04* (2013.01); *G06N 3/08* (2013.01); *G16H 50/30* (2018.01)

(58) Field of Classification Search
CPC .......... G06K 7/10366; G06K 7/10009; G06K 19/0723; G06K 7/10316; G06K 7/10356; G06K 7/0008; G06K 19/0717; G06K 7/10257; G06K 7/10128; G06K 19/07749
USPC ....................................................... 340/10.1
See application file for complete search history.

(56) References Cited

U.S. PATENT DOCUMENTS 7,158,030 B2  1/2007  Chung
7,388,506 B2  6/2008  Abbott
(Continued)

OTHER PUBLICATIONS

Ann Grackin et al., "RFID Hardware: What You Must Know", RFID Technology Series, Jun. 2006.
(Continued)

*Primary Examiner* — Mark S Blouin
(74) *Attorney, Agent, or Firm* — Culpepper IP, LLLC; Kerry S. Culpepper

(57) ABSTRACT

A system includes a data collection engine, a plurality of items including radio-frequency identification chips, a plurality of third party data and insight sources, a plurality of interfaces, client devices, a server and method thereof for preventing suicide. The server includes trained machine learning models, business logic and attributes of a plurality of patient events. The data collection engine sends attributes of new patient events to the server. The server can predict a suicide risk of the new patient events based upon the attributes of the new patient events utilizing the trained machine learning models. Using business logic, data visualization and the trained machine learning models, the server can also make recommendations to reduce the risk of suicides.

16 Claims, 28 Drawing Sheets

Related U.S. Application Data now Pat. No. 9,679,108, which is a continuation of application No. 15/004,535, filed on Jan. 22, 2016, now Pat. No. 9,569,589.

(60) Provisional application No. 62/113,356, filed on Feb. 6, 2015.

(56) References Cited

U.S. PATENT DOCUMENTS

| | | | |
|---|---|---|---|
| 7,479,887 B2 | 1/2009 | Meyer | |
| 7,586,417 B2 | 9/2009 | Chisholm | |
| 7,772,981 B1 | 8/2010 | Lambert et al. | |
| 7,850,893 B2 | 12/2010 | Chisholm et al. | |
| 7,852,221 B2 * | 12/2010 | Tuttle | G06K 7/10346 340/10.1 |
| 7,875,227 B2 | 1/2011 | Chisholm | |
| 7,922,961 B2 | 4/2011 | Chisholm et al. | |
| 7,973,664 B1 | 7/2011 | Lambert et al. | |
| 8,097,199 B2 | 1/2012 | Abbott et al. | |
| 8,098,162 B2 | 1/2012 | Abbott et al. | |
| 8,120,484 B2 | 2/2012 | Chisholm | |
| 8,181,875 B2 * | 5/2012 | Nishido | G06K 19/0701 235/451 |
| 8,212,226 B2 | 7/2012 | Chisholm | |
| 8,296,247 B2 | 10/2012 | Zhang et al. | |
| 8,478,535 B2 | 7/2013 | Jojic et al. | |
| 2010/0190436 A1 | 7/2010 | Cook et al. | |
| 2011/0291809 A1 * | 12/2011 | Niemiec | A61B 5/0002 340/10.1 |
| 2013/0002034 A1 | 1/2013 | Onizuka et al. | |
| 2013/0246207 A1 | 9/2013 | Novak | |
| 2015/0317589 A1 | 11/2015 | Anderson et al. | |
| 2017/0370734 A1 | 12/2017 | Cojin | |
| 2018/0032690 A1 | 2/2018 | Perlman | |

OTHER PUBLICATIONS

Lyngsoe Systems, "PR34 X—Belt Loader RFID Reader User Guide", Apr. 16, 2016.

Lyngsoe Systems, "ADM User Manual", Sep. 21, 2010.

Pivato et al., "Experimental Assessment of a RSS-based Localization Algorithm in Indoor Environment", [online], May 2010 [retrieved on Sep. 4, 2015]. Retrieved from the Internet: <URL:http://www.researchgate.net/profile/Paolo_Pivato/publication/224146714_Experimental_Assessment_of_a_RSS-based_Localization_Algorithm_in_Indoor_Environment/links/0912f502b6b29f22ea000000.pdf>.

Zafari et al., Micro-location for Internet of Things equipped Smart Buildings, [online], Jan. 7, 2015 [retrieved on Sep. 3, 2015]. Retrieved from the Internet<URL:http://arxiv.org/abs/1501.01539>.

Bolic et al., "Proximity Detection with RFID: A Step Toward the Internet of Things", Apr. 23, 2015, Pervasive Computing IEEE, vol. 14 Issue:2, Published by IEEE.

Wong et al., "30 Years of Multidimensional Multivariate Visualization", [online], 1997 [retrieved on Aug. 12, 2016]. Retrieved from the Internet: <URL:http://citeseerx.ist.psu.edu/viewdoc/download?doi=10.1.1.30.4639&rep=rep1&type=pdf>.

Impinj, White Paper "New Thinking on an Old Challenge: Improving Healthcare Asset Management with RAIN RFID Technology", [online], 2017 [retrieved on Nov. 16, 2017]. Retrieved from the Internet: <URL:https://www.impinj.com/media/2046/impinj-healthcare-asset-management-white-paper.pdf>.

Erica Drazen, "Using Tracking Tools to Improve Patient Flow in Hosptals", [online], Apr. 2011 [retrieved on Feb. 15, 2018]. Retrieved from the Internet: <URL:https://www.chcf.org/publication/using-tracking-tools-to-improve-patient-flow-in-hospitals/>.

Leaf Healthcare, White Paper "Technical Overview of the Leaf Patient Monitoring System", [online], 2018 [retrieved on Mar. 19, 2018]. Retrieved from the Internet: <URL:http://www.leafhealthcare.com/pdfs/LH_WP_TechOverview_1564AB_030818.pdf>.

Leaf Healthcare, "A New Standard for Optimizing Patient Repositioning", [online], 2018 [retrieved on Mar. 19, 2018]. Retrieved from the Internet: <URL:http://www.leafhealthcare.com/solution.cfm#s6>.

Suzanne Hodsden, "Smith & Nephew Integrates Wireless Patient Monitoring Into Wound Care Platform", MED Device Online, [online], Apr. 10, 2017 [retrieved on Mar. 19, 2018]. Retrieved from the Internet<URL:https://www.meddeviceonline.com/doc/smith-nephew-integrates-wireless-patient-monitoring-into-wound-care-platform-0001>.

Robert R. Althoff, MD, PhD, "Suicide Risk Assessments in Hospitals Using Systematic Expert Risk Assessment for Suicide (SERAS)", [online], Jun. 5, 2018 [retrieved on Jul. 7, 2018]. Retrieved from the Internet: <URL: http://vtspc.org/wp-content/uploads/2018/06/Althoff-VT-Suicide-Prevention-Symposium-Presentation-6-4-18.pdf>.

* cited by examiner

Data Fields/Properties

|  | Property 1 | Property 2 | Property 3 | ... | Property N |
|---|---|---|---|---|---|
| Data 1 |  |  |  |  |  |
| Data 2 |  |  |  |  |  |
| Data 3 |  |  |  |  |  |
| ... |  |  |  |  |  |
| Data N |  |  |  |  |  |

Collected Data

FIG. 15

Value Plotted on Actual Range
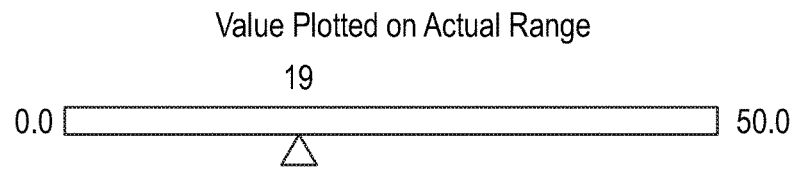
FIG. 16
Equivalent Value Plotted on Normalization Scale
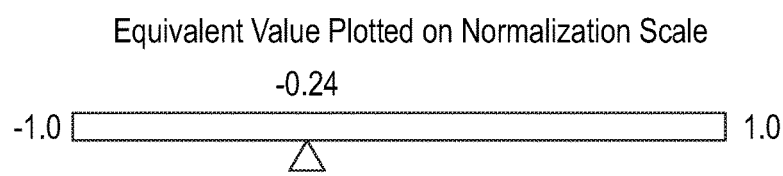
FIG. 17
One-of-N Encoding
| Discharging Specialty |
|---|
| Hospital Medicine |
| General Surgery |
| Orthopedic Surgery |
Encoding →
| Discharging Specialty |
|---|
| 1.0, 0.0, 0.0 |
| 0.0, 1.0, 0.0 |
| 0.0, 0.0, 1.0 |
FIG. 18
Equilateral Encoding
| Discharging Specialty |
|---|
| Hospital Medicine |
| General Surgery |
| Orthopedic Surgery |
Encoding →
| Discharging Specialty |
|---|
| 0.5, 1 |
| 0.933, 0.25 |
| 0.06698, 0.25 |
FIG. 19

Exemplary Regression Task-Supervised Learning
(2D Example Shown for Simplicity)

Actual vs. Predicted on Pre-existing Data

— Actual
----- Predicted

Forecasting Using Temporal Data

Past | Future

SYSTEM, SERVER AND METHOD FOR PREVENTING SUICIDE

CROSS-REFERENCE TO RELATED APPLICATIONS

The present application is a continuation of U.S. patent application Ser. No. 15/950,060 filed on Apr. 10, 2018, which is a continuation-in-part of U.S. patent application Ser. No. 15/891,114 filed on Feb. 7, 2018, which is a continuation-in-part of U.S. patent application Ser. No. 15/704,494 filed on Sep. 14, 2017 now U.S. Pat. No. 9,928,342, which is a continuation-in-part of U.S. patent application Ser. No. 15/592,116 filed on May 10, 2017 now U.S. Pat. No. 9,848,827, which is a continuation of U.S. patent application Ser. No. 15/390,695 filed on Dec. 26, 2016 now U.S. Pat. No. 9,679,108, which is a continuation of U.S. patent application Ser. No. 15/004,535 filed on Jan. 22, 2016 now U.S. Pat. No. 9,569,589, which claims the benefit of U.S. Provisional Patent Application No. 62/113,356 filed on Feb. 6, 2015, the contents all of which are incorporated herein by reference.

TECHNICAL FIELD

The technical filed generally relates to a system including a client device, data input sources and a server.

BACKGROUND

A Radio-frequency Identification (RFID) chip can transmit information to a reader in response to an interrogation signal or polling request from the reader. The RFID chip can be incorporated in a tag (RFID tag) which is placed on a medical consumable item so that information can be passively captured. An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some medical consumable items may not be feasible do to financial considerations, weight, etc. On the other hand, placing a passive-type RFID tag on medical consumable items may be more feasible; however, a power source will be needed to passively obtain information. Therefore, a device that can provide power to the RFID tag on the medical consumable item as well as obtain the information from the RFID tag would be beneficial.

Artificial Intelligence (AI) technologies such as machine learning and deep learning have become ever present due to technological advances in data storage and processing. Machine Learning at its most basic is the practice of using algorithms to parse data, learn from it, and then make a determination or prediction about something in the world. So rather than hand-coding software routines with a specific set of instructions to accomplish a particular task, the machine is "trained" using large amounts of data and algorithms that give it the ability to learn how to perform the task. Deep learning involves neural networks inspired by our understanding of the biology of our brains all those interconnections between the neurons. But, unlike a biological brain where any neuron can connect to any other neuron within a certain physical distance, these artificial neural networks have discrete layers, connections, and directions of data propagation.

SUMMARY

It is very important to identify, diagnose and treat medical, operations, and administrative issues that may not be easily apparent during medical care to enable better care coordination, quality improvement, care surveillance, monitoring, and clinical business intelligence. However, medical care for patients is often provided among multiple providers in a plurality of care settings that may have no affiliation. In addition, a large number of the determinants of health and wellness are socio-economic in nature—social determinants of health—which may not be adequately captured in traditional healthcare information systems. For this reason, third party data sources and sensor-based data have the potential to significantly augment insight to providers of healthcare and care coordinators. Certain risk factors may be known to organizations providing some services, but those risk factors may not be known to other organizations providing other services. For example, medical care for a veteran may be spread across multiple care providers. One risk factor may be known to one care provider and another risk factor known to another care provider. Another example would be in a case where a social worker may be providing help with unemployment and not be aware of medication the patient is taking that increases suicidal thoughts.

A system that can identify patients at risk for suicide and scenarios that may represent increased risk that a patient may commit suicide would be desirable. It would be further preferable if such a system could take advantage of AI techniques to predict the risk that a patient may commit suicide so that resources can be allocated to those at highest risk for suicide, thereby reducing suicides. Those resources could be provided to help deal with suicidal ideation, suicidal behavior, and suicides for example.

Without counter-measures, suicidal patients might only be identified when presenting due to the sequelae of suicidal ideation and or behavior or when an individual or provider asks a patient if they are suicidal and the patient honestly answers. In view of this concern, the present disclosure concerns a system capable of predicting whether a patient may be having suicidal ideation or may be about to actively be engaged in suicidal behavior using methodologies.

Accordingly, the present disclosure concerns a system which provides a platform for collecting data and analyzing data collected over time and in real time using trained models to deliver actionable insights in real time to the appropriate stakeholders capable of intervening.

The system can leverage analytics from third party data sources as inputs into its predictive analytics, such as the Department of Veteran's Affairs Reach Vet Analytics that can be used to assess and or predict the risk of suicide, for example.

The system receives and delivers information to and from hospital information systems and client devices used by healthcare and social services workers, patients, family members, and care givers. In addition, the system provides client applications for managing patients identified to be at high risk for suicide, clinical and administrative suicide prevention work flows, real time analytics and data visualization tools that aid provider organizations and their healthcare worker employees in carrying out these work flows, monitoring these work flows, and improving the quality and timeliness of the services delivered as a part of this work flow. The improvement of the quality and timeliness of services is namely aimed at preventing suicide when a patient has been identified to be at high risk.

Furthermore, the system improves the provider organization's situational awareness, responsiveness to particular situations or scenarios that pose risk, and compliance with key performance indicators of the inventive system's proprietary technology enabled workflows. Situational awareness, notifications and escalations thereof leverage the inventive system's notification micro service.

The system is notably unique in not only predictive analytics but also in its capability to inject its insights, findings and predictions into key clinical and administrative work flows enabled by the system's client applications that are used to manage patients identified to be at high risk for suicide and aid in the management and monitoring of their care within and across a plurality of healthcare provider organizations, such as in the case of "non-Veterans Affairs care" also known as "non-VA care." The system can utilize data collected in the course of work flows carried out via its client applications as inputs into to its predictive analytics.

Accordingly, the present disclosure concerns a system comprising: a plurality of radio-frequency identification (RFID) chips, wherein a first RFID chip of the plurality of RFID chips is a passive-type RFID chip, and one or more of the plurality of RFID chips include a sensor group; a data collection engine (DCE) device communicating with the first RFID chip, wherein the DCE comprises: a power transmission subsystem including a power source and an antenna arranged to wirelessly transmit power from the power source to the first RFID chip; a transceiver configured to receive first data from at least one of the first RFID chip and a second RFID chip of the plurality of RFID chips while the first RFID chip is activated by the power received, the first data including identification information of the at least one of the first and second RFID chips; a controller operatively coupled to the transceiver; and one or more memory sources operatively coupled to the controller, the one or more memory sources including instructions for configuring the controller to generate one or more messages indicative of the identification information to be sent by the transceiver to a server device via the network connection, wherein the first RFID chip includes an antenna for wirelessly receiving the power from the transceiver of the DCE and control logic for generating the identification information, wherein the server device comprises: a transceiver configured to receive the one or more messages from the DCE; a controller operatively coupled to the transceiver; and one or more memory sources operatively coupled to the controller, the one or more memory sources storing a trained neural network model (NNM) for generating an output value corresponding to a present event based upon one or more of the identification information and position information, wherein the output value corresponds to a suicide risk.

The present disclosure further concerns a client device comprising: a transceiver communicating with a server device via a connection to a network, the transceiver configured to send a request message to the server device and receive a reply message from the server device in response to the request message, the reply message including an output value generated from a trained model stored at the server device; a controller coupled to the transceiver; a display device coupled to the controller; and a memory including instructions for configuring the controller to: generate the request message; and render a graphical display on the display device based upon the output value. The reply message can include a plurality of output values, the graphical display is a cluster diagram including a plurality of clusters of similar characteristic output values of the plurality of output values.

The controller is further configured to: calculate a suicide prevention readiness score (SPRS) from a trained model based upon an input data set; and generate an information reply including a graphical display indicating the output value of trained model.

The input data set can include a status of healthcare provider organization personnel suicide prevention training and attributes of the suicide prevention training, and a status of a healthcare provider organization community outreach activities and attributes of the healthcare provider organization community outreach activities.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIG. 15 is an illustration of an exemplary data set for patient attributes for various patient events.

FIGS. 16-17 are illustrations of various exemplary approaches for normalizing the data set.

FIG. 18-19 are illustrations of various exemplary approaches for encoding the normalized data set.

DETAILED DESCRIPTION

In overview, the present disclosure concerns a system which includes various input data sources, client devices and backend devices. The input data source may include a Data Collection Engine (DCE) and an RFID tag associated, for example, identifications of medical professionals and patients. The backend devices can be one or more server devices.

The instant disclosure is provided to further explain in an enabling fashion the best modes of performing one or more embodiments. The disclosure is further offered to enhance an understanding and appreciation for the inventive principles and advantages thereof, rather than to limit in any manner. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
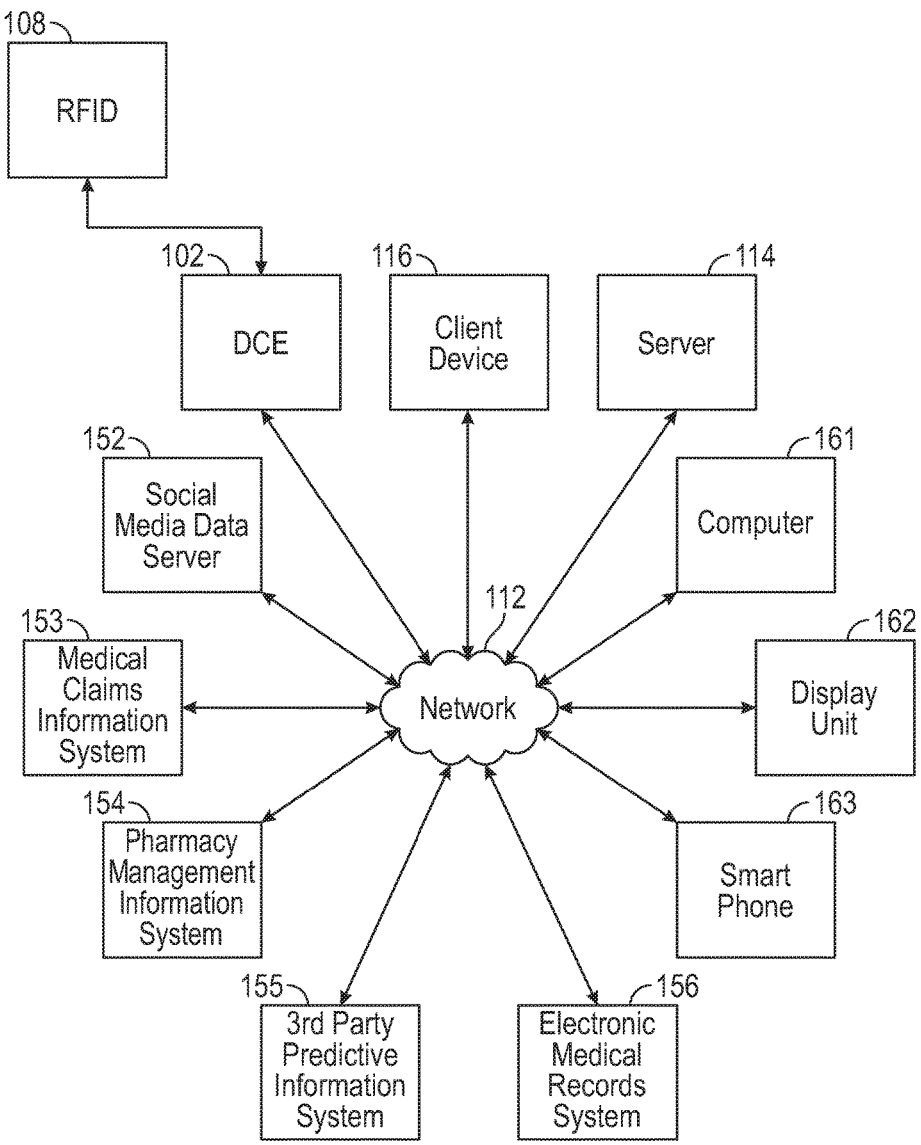
FIG. 1 illustrates an exemplary core operating environment in which the portions of the system communicate via a connection to a network.

Referring to FIG. 1, an exemplary operating environment in which the system according to various embodiments can be implemented will be discussed. The environment includes various input data sources such as a DCE 102, social media data server 152, medical claims information system 153, a pharmacy management information system data 154, third party predictive information system data 155, and an electronic medical records system data 156. The system is also capable of utilizing data originating from cameras, video sensors and even closed-circuit television and similar technologies in conjunction with facial recognition technology and facial expression analysis for emotion and behavior prediction as inputs into its predictive models. The system can also use various data inputs and changes therein over time.

Some exemplary examples of data inputs are healthcare data from a variety of sources. Some data such as vital signs can be observed directly from the patient. The vital sign data would then be inputted into the system by an end user using a client application for example. Healthcare data can also be obtained from other sources such as data input from users that use client applications that comprise the inventive system or that from third party applications or systems, a healthcare information exchange (HIE), hospital information systems, patient facing software applications, Health level 7, continuity of care documents (CCDs), Recovery Engagement and Coordination for Health—Veterans Enhanced Treatment (REACH-VET) analytics and data, Army Study to Assess Risk and Resilience in Servicemembers (Army STARRS) analytics and data, third party methods or algorithms, medical claims information submitted for payment of services rendered, consults for healthcare services, status changes related to the fulfillment of consult requests, the content of consult requests and the reports received in response, medical imaging data and interpretations thereof, laboratory data results, healthcare transportation records and claims for payment remittance for such services, known prior suicide attempts, pharmacy prescription and pharmaceutical dispensing data, and data from standardized patient assessments such as SF-36.

Other data can also come from sources such as 911 call centers, police scanners, law enforcement databases, social media data, human facial imaging data and changes over time and interpretations thereof, location data, attributes describing a patient's living situation, economic data from the patient's location such as the unemployment rate, attributes of the patient such as marital status, race, etc. . . . , data collected from care givers, family members and friends of the patient, data that may be indirectly attained such as data about job loss, behavior changes, or relationship changes, obituaries, death certificate data, news articles from various media sources and Internet of things (IoT) enabled devices for example. The sources of data are not limited as long as there is predictive value in the data.

Figure 10:
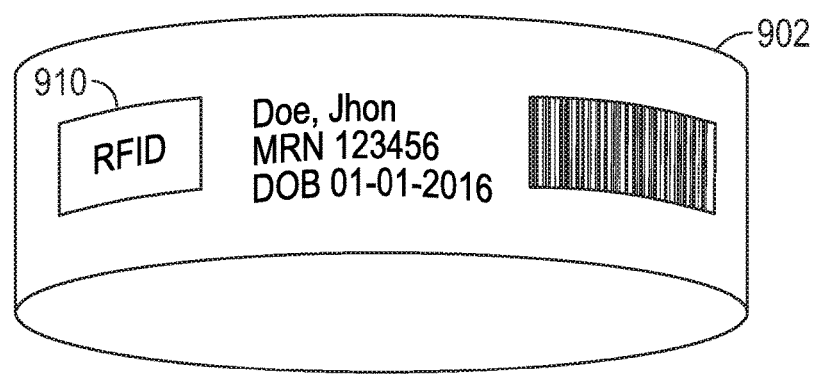
FIG. 10 is an illustration of a patient wrist band including an RFID tag.
Figure 11:
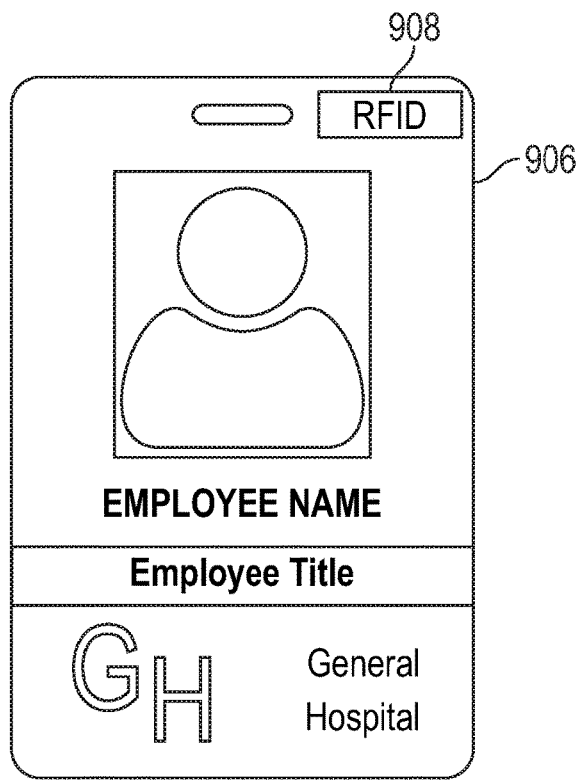
FIG. 11 is an illustration of a medical professional identification including an RFID tag.

The DCE 102 is shown communicating with an RFID tag 108. As discussed later, the DCE can be disposed in one or more rooms of a facility such as a hospital and the RFID tag 108 can be associated with a medical item such as a patient wrist band 902 (FIG. 10) or doctor ID badge 906 (FIG. 11). The communication between the RFID tag 108 and the DCE 102 is preferably wireless; however, wireline communication or a combination of wireless and wireline communication can also be used in some cases. Moreover, the system likely includes many DCEs. The DCE 102, as well as all of the data input sources, can communicate with one or more server devices (represented generally by and referred to hereon as "server") 114 via a connection to a network 112 such as a local area network (LAN), wide area network (WAN), the Internet, etc. A client device 116 can communicate with the server 114 and the DCE 102 via a connection to the network 112. Another computing devices such as computer 161, display unit 162 and smartphone 163 also communicate with the server 144 via the connection to the network 112. All communication can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. One of ordinary skill in the art should appreciate that the server 114 can represent entities necessary for providing cloud computing such as infrastructure and service providers.

Figure 2:
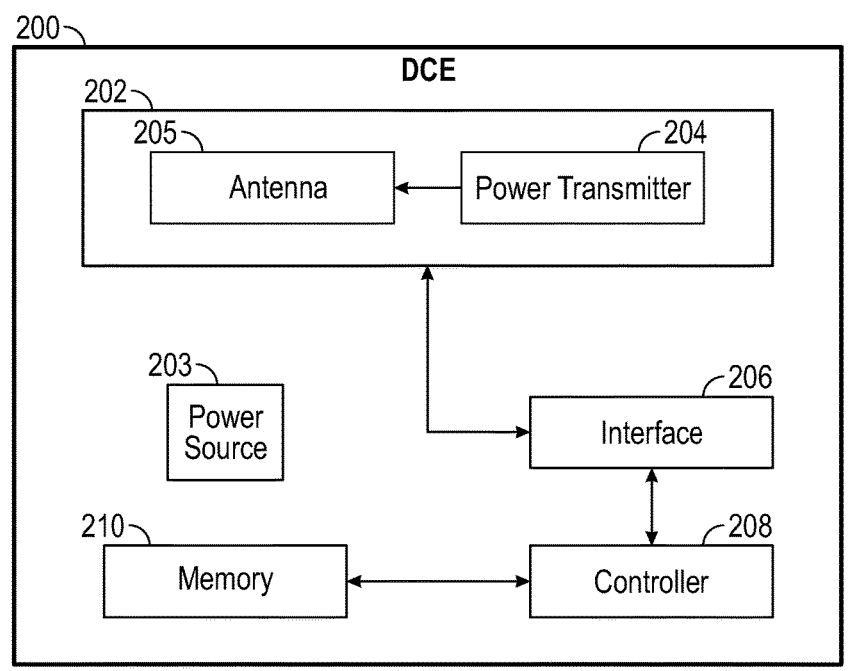
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of medical data and events received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

In FIG. 1, the DCE 102 is shown communicating with RFID tag 108. However, other devices such as smartphone 163, for example, can also communicate with the RFID tag.

Figure 3A:
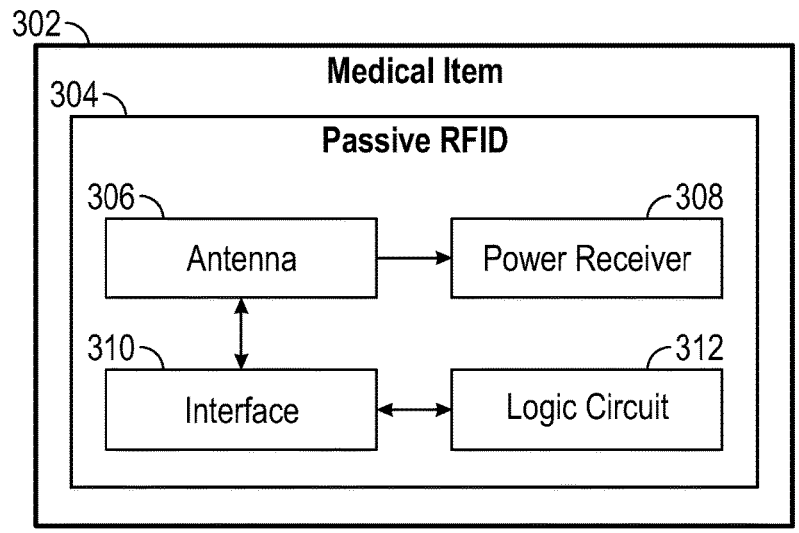
FIG. 3A is a block diagram illustrating exemplary portions of a passive-type RFID tag.

Referring to FIG. 3A, portions of an exemplary passive-type RFID tag 304 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates data such as an identification of the RFID tag and/or the item to which it is affixed, state, location, and changes in any data or properties thereof over time, all of which will be referred to as medical data. It should be noted that the data includes situational data which refers to a) the identity of the RFID tag, the identity reference for an individual, facility plant, property, equipment to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the medical data received from the logic circuit 312 into an appropriate format for transmission. For example, the interface 310 can demodulate ASK signals or modulate data from the logic circuit 312 into ASK signals.

Figure 3B:
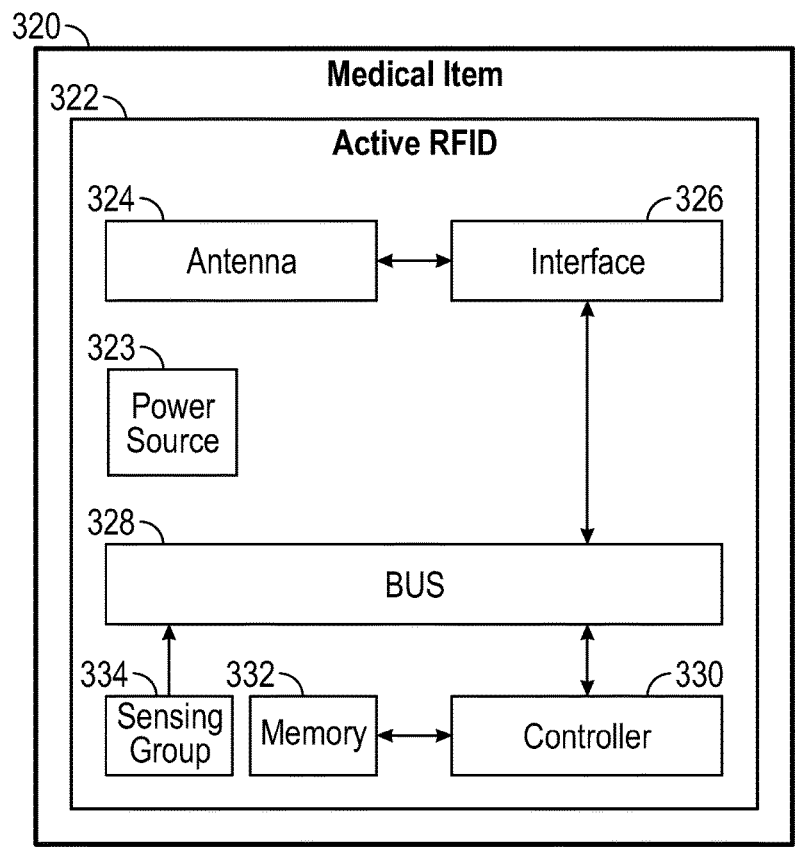
FIG. 3B is a block diagram illustrating exemplary portions of an active-type RFID tag.

Referring to FIG. 3B, circuit-level portions of the active-type RFID tag 322 on a medical item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the chip is within a predetermined distance from another RFID tag, a distance from one or more other RFID tags and/or the DCE, and/or distance and angle from a baseline orientation. The sensing group 334 can include a set of accelerometers for determining the acceleration value of the item 320, a digital compass that collects orientation information about the item 322, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass and/or the gyroscope, can facilitate motion detection. The sensing group 334 can include a separate OpenBeacon active tag or a Sense-a-Tag as described in "Proximity Detection with RFID: A Step Toward the Internet of Things" by Bolić et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another tag. Particularly, the controller 330 can be configured to send a registration message which includes identification data associated with the RFID tag 322 and thus the medical item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference. As mentioned above, the DCE 102 can store data regarding its fixed location (i.e. room 106). In this case, the physical location of the RFID tag 110 can be determined via the DCE 102. Alternatively, the RFID tags can obtain position from some external reference (i.e. a device with GPS or via a device that provides an indoor positioning system location reference, or WiFi hotspots, that themselves have a known location, which can somehow transmit WiFi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 4:
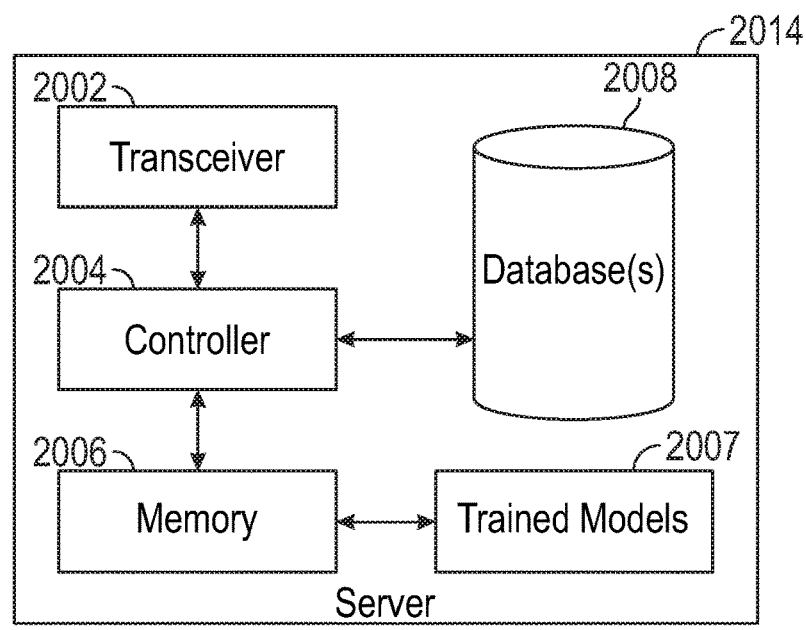
FIG. 4 is a block diagram illustrating exemplary portions of a server according to an embodiment.

Referring to FIG. 4, the server 2014 includes a transceiver 2002, a controller 2004, a first memory portion 2006, a second memory portion 2007 and one or more databases stored in another memory source depicted generally by database 2008. The transceiver 2002 can be similar to the transceiver of the DCE. The transceiver 2002 receives data via the network from the DCE, data retrieval requests from the client device 116 and sends replies to the data retrieval requests. The databases 1108 can include an item database, a patient database, and a medical professional database. That database can be, for example, an atomic data store. The transceiver 1102 receives data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 1102 sends the information reply including the usage parameters associated with the one or more RFID chips to the client device. The transceiver 1102 can be similar to the transceiver of the DCE.

The memory portions 2006, 2007, 2008 can be one or a combination of a variety of types of memory such as RAM, ROM, flash memory, DRAM or the like. The memory portion 2006 includes instructions for configuring the controller 2004. The second memory portion 2007 includes one or more trained models. It should be noted that the database and the trained models can be included in the memory portion 2006. They are shown separately here in order to facilitate discussion. The data inputs as discussed above are collectively stored the database 2008.

The controller 2004 is configured according to the instructions in the first memory portion 2006 to determine data in the database 2008 that is associated with the identification for each of the one or more RFID tags (received in the message from the DCE); store data in the message from the DCE in the database 2008 to be associated with the identification of the first RFID tag; and as will be discussed more fully below, predict a suicide risk associated with a patient event based upon inputting attributes of the patient event into the trained model such as a neural network model or self-organizing map network.

The controller 1104 and database 1108 can be configured to perform command query responsibility segregation in which commands are separated from queries to allow scaling of servers that respond to queries separately from servers delegated to responding to messages. The controller 1104 and database 1108 can further be configured to use event sourcing and/or event streaming to ensure all changes to an application state get stored as a series of events which can be not only queried but reconstructed.

Figure 5:
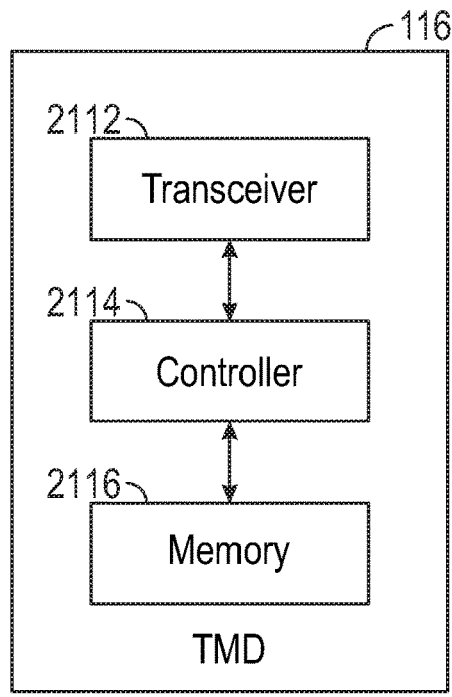
FIG. 5 is a block diagram illustrating exemplary portions of a client device.
Figure 7:
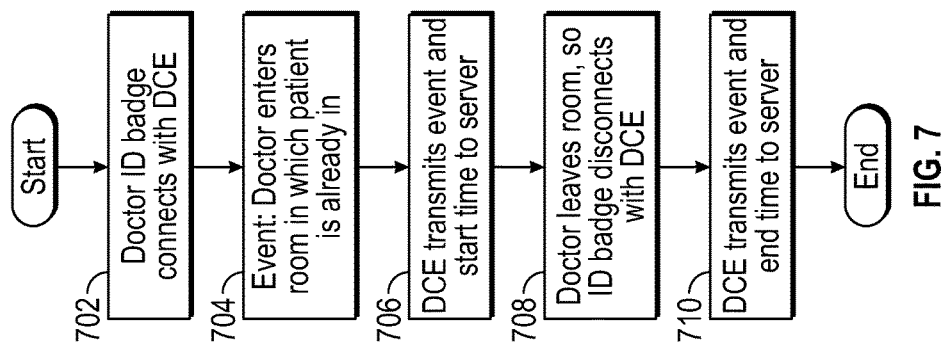
FIG. 6-7 are flow diagrams illustrating exemplary operations of the system.

Referring to FIG. 5, the client device 116 includes a transceiver 2112, a controller 2114 and memory 2116. The transceiver 2112 can be similar to the transceiver of the DCE. The transceiver 2112 receives information or resource requests such as, for example, http requests, via the network, from other client devices and other data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of patient events. The transceiver 2112 sends an information reply. The controller 2114 is configured according to instructions in the memory 2116 to generate either solely visualization data (i.e. a json object) or graphical displays (i.e. html markup and javascript) including visualization data retrieved from server 2014 as the information reply that can then be used to generate a display on the client device. For example, the graphical display can indicate a Suicide Prevention Readiness Score.

In the discussion here, the server 2014 and client device 116 are shown as separate entities for ease of discussion. However, in actual implementation the server 2014 and client device 116 may be implemented within a single computing device. Moreover, the portions of server 2014 may be distributed among various computing devices. For example, the trained models shown stored in memory portion 2007 or the database(s) 2008 could be stored at a plurality of different computing devices. Modifications as described above and below to the embodiments may be combined and are not limiting to the inventive system.

The system can also use work flows as inputs, data collected in the process of managing patients done via the proprietary user interfaces as well as data derived from activity tracked via the hospital information systems; some examples of the latter include appointments, patient movements, facility visits or admissions, healthcare employee charting, among others.

Examples of the work flow specific client applications include, applications used by social workers and clinicians that manage patients at high risk for suicide and client applications that the managers and facility administrators that oversee this clinical and administrative work flow use. The system's client applications, used on both mobile and desktop devices, include both native and web browser based technologies that leverage the organic data collected over time from use of the system, the system's server's hospital information system and healthcare information exchange interfaces and the other numerous interfaces providing data input into the system and the predictive analytic outputs of the proprietary models that consume this data. Data generated via these work flows executed in the client application in the regular course of its use and data about the facility or provider organization that is responsible for managing a given patient at high risk for suicide is used not only to manage the patient's care but also as inputs to the system's predictive analytics.

Some examples of data the system collects and leverages include: i) any patient record flags from hospital medical records and any reviews thereof, renewals, discontinuations and related documentation, for example documentation explaining the basis for continuance or discontinuation; ii) healthcare or social services worker charting including, but not limited to social worker charting, physician and psychologist charting, suicide prevention safety plans, patient risk assessments and other charting including, but not limited to: a) metadata about the charting such as note title, date of creation, date signed by author or cosigners, identity of author and any cosigners; and b) content of such charting both structured and free text; iii) any appointments the patient has scheduled for medical or social services; iv) hospital information system registration and patient movement data from medical facilities, both the local facility and remote facilities via healthcare information exchange. For example, did the patient go to a given medical facility for a scheduled appointment, did the patient no show for an appointment, was the patient seen in the emergency department, and/or was the patient admitted to an inpatient facility; v) any follow up activities that take place such as following up patients with particular patient record flags and documentation occurring at that time or thereafter such as in the event a patient does not show up for an appointment, or in the event a patient checks out after an appointment, is discharged from the emergency department or is discharged from an inpatient facility. Utilizing proprietary business logic and analytics, the system can identify situations that may represent a change or increase in the risk of a potential suicide and when such scenarios are identified, escalate this concern to the appropriate stakeholders.

Some simple examples of non-patient specific data the system utilizes in its analytics and provides client based work flow solutions to help provider organizations manage includes, but is not limited to, the status of suicide prevention training by employees at a given provider organization or facility (i.e., was it completed within a certain range of time from hire and/or was it renewed/updated at a predefined interval as well as the nature of or attributes of the suicide prevention training completed) and attributes about the suicide prevention outreach conducted by the facility or provider organization (frequency, location, partner organizations involved, attendance, attendees, speakers/presenters, etc.) and changes in these attributes over time. One can think of these as "attributes of the facility" that are input into the analytics when a patient at high risk for suicide is being managed at a given facility both at the time of model training (i.e. the attributes as assessed previously in conjunction with antecedent cases) and subsequently for de novo cases for which suicide risk is being predicted.

In addition to: i) the system's client applications end users use to manage this work flow; and ii) the use of this organically generated data as inputs into the training of the system's predictive models, the system also provides within its client applications functionality that allows the facility to track the status of suicide prevention training for its employees and to monitor how frequently it is carrying out suicide prevention outreach and the quality of said outreach activities based on predefined key performance indicators. The system does this by including a client application that generates outputs to a graphical user interface presenting data visualizations, score cards, and dashboard metrics describing the data generated from these activities, the individuals involved, and the related key performance metrics; specifically, notable trends in these at snapshots in time and over time. Along with these aggregate statistics and key performance indicators, the system provides a proprietary scoring of the facility, dubbed the facility's "Suicide Prevention Readiness Score (SPR Score or SPRS)." The SPRS is assessed over time and in real time and trends and data visualization views of the score and its subcomponents over time are provided. Using controls in the graphical user interface, end users can change the date ranges and roll up (aggregate) or drill down into (examine sub-groups) the data and regenerate the data visualizations, score cards, and dashboard metrics after defining new criteria (ad-hoc queries). In this way, the system allows its end users to ask questions of their data assessing their performance in carrying out the activities entailed in this work flow. The system can also be configured to notify particular stakeholders using its notification micro service as described elsewhere herein, when particular key performance metric variances are identified relative to benchmarks or predefined thresholds. The SPRS could then be an input for patient when receiving services at the facility.

For those patients at high risk for suicide that have all or some of their medical and mental healthcare services rendered at more than one provider organization, the system is able to utilize health care information exchange and medical claims data to track the patient's care and milestones in their care, events and various clinical and administrative endpoints that feed into the systems' predictive analytics. Moreover, for some provider organizations (for example the Veterans Healthcare Administration) that outsource and which may pay for care delivered under contract by other providers in the community or for entities engaged in management of their patient's care across multiple facilities (payors or provider organizations using value based care delivery models, for example), the system also has native and web based client applications usable on mobile and desktop devices (as well as API interfaces that can be integrated into by 3rd party developers) that can be leveraged to further enhance or supplement the data received via health information exchange, Continuity of Care Documents (CCD), and claims data.

Alerts and Notifications

The system consists of machine learning based predictive analytics that assess the probability that a given patient will commit suicide. The system is capable of not only calculating the risk, but also deploying and or transmitting its findings to various stakeholders. The system is further capable of providing real time analytics about patients that have been identified to be at risk and changes in their status or attributes of their medical care and services over time. The system includes proprietary workflow technology that can be employed by healthcare provider organizations to better manage patients that have been identified to be at risk for suicide and provides real time analytics and insight regarding key performance metrics related to this proprietary workflow technology.

The system can provide alerts via any number of communication mediums when particular tasks are soon to be due, due or past due or when certain events have been predicted to occur with a probability greater than the configurable threshold levels. Further, the system provides analytics that summarize how well the provider organization, its subdivisions or teams, and its individual healthcare and social services workers are performing currently and over time in managing patients at risk for suicide via this proprietary end user client technology enabled workflow, including performance, process and outcome measures. Further data collected, and statistical trends derived from this data is used as input data to the inventive systems predictive analytics.

The system is also able to be configured to send out automated communications (notification micro service) and alerts following proprietary business rules and logic to a variety of client devices to native applications running on hardware devices via a variety of communications technologies, protocols and networks. Examples of hardware devices that could be used are laptops, desktops, thin clients, tablets, phones, pagers and other mobile devices. The automated communications, notifications, and alerts terminology may be used interchangeably. The output value of the system may be an automated communication for one end user, a notification for another end user and an alert for a third end user. The business rules would define how the communications of the inventive system are sent out.

The system's notification micro service can be configured to notify and escalate, if necessary, situations or scenarios that warrant attention by specific stakeholders based on the proprietary predictive models (i.e. trained neural network predictive models), business logic, administrative rules, and clinical pathways the system leverages. In the event such a scenario is identified, the notification micro service can leverage any number of communication technologies to alert stakeholders and end users, for example, but not limited to, automated phone calls, email, SMS messages, analog or digital paging systems, push notification, audible and tactile alerts, visual alerts (i.e. in the system's client applications), HTTP (i.e. post to an internal or 3rd party system), HL7, overhead announcement via hospital PA system.

The system can be configured to send out particular communications or requests and to request the submission of (a reply with) particular predefined data (for example via a form which may request structured data or allow the entry of free text data) in response—in many ways this is analogous to customer satisfaction surveys that may be sent out after, for example a hotel stay at a particular hotel operator's property. As with other use cases described herein, data collected in this process is used as an input to the systems predictive analytics (i.e. the aggregate patterns over time therein, particularly from antecedent cases with known outcomes—suicide/no suicide) and help the system better predict outcomes related to the two endpoints of interest over time. In this way the system is a platform that can be employed to address the needs of particular provider organizations such as the Veterans Health Administration that have a vested interest in preventing suicide among US Veterans, but that face challenges in doing so given only a subset of Veterans receive healthcare services at a Veterans Health Administration facility.

Patient facing native and web browser-based client applications could be used to securely communicate with the patient and that enable secure communication between and amongst the patient, care givers, healthcare workers, social services workers, and other stakeholders in the patient's care and wellbeing.

Authentication and Authorization

Access to the system is secure and requires authentication and authorization and data communications are encrypted. The system's end user functionality can be accessed via desktop workstation or mobile device and can be via the system's client applications running in a web browser or via the system's native applications running on a mobile or desktop device. The system's user interfaces adapt to a variety of device form factors and viewport sizes.

The system and its related client applications have the ability to encrypt and decrypt data as needed for to execute necessary business processes and logic and for presentation of data to authenticated and authorized users in the user interfaces of the systems client applications.

Access to the system's client application-based workflow and communications solutions and dashboard and data visualization technologies is controlled using state of the art access control technologies via which users are authenticated and authorized, for example, OAuth2/claims based security, OpenIdConnect, etc. The system also can be configured to use enterprise access control systems, for example, but not limited to, Lightweight Directory Access Protocol (LDAP), the Department of Veterans Affairs Citrix Access Gateway (CAG), Personal Identity Verification (PIV) Card, and/or Access/Verify based authorization/authentication. In addition, the system can be configured to work with single sign on technologies.

Data sent and received by the system is encrypted in motion and at rest and can be configured to use current and future state of the art encryption methodologies such as Triple Data Encryption Standard (DES), the Rivest-Shamir-Adleman (RSA) cryptosystem, Blowfish, Two Fish, Advanced Encryption Standard (AES), among others.

Data Visualization and Client Application

The system provides data visualization technologies, briefly described above, to enable its users to observe trends, easily assess the current status of particular processes or work flows versus targets/thresholds/reference ranges, all in real time. The system utilizes business rules, graphics, charts, the visual presentation of statistical process control analytics, icons, animation, color and text to highlight particular information. The dashboard makes current trends available and provides inputs and controls that enable "drill down/roll up" and "slice and dice" features that leverage attributes of the input data and metrics; this provides ad hoc query functionality that allows end users to examine data, metrics, and key performance indicators in aggregate and/or for particular sub groups over configurable date ranges. The system can be configured to send out, for example via email, periodic reports that detail performance and trends over time. For example, multiple teams of healthcare workers at a given facility or across multiple facilities may be tasked with managing particular patients at high risk for suicide. The system's work flow tools and analytics in conjunction with end user configuration can determine which teams and individuals are responsible for managing the care of a given patient at high risk for suicide. Leveraging this knowledge, the system provides proprietary scoring of performance in aggregate, for each team, and for each individual. Because particular aspects of the system's proprietary technology enabled monitoring of specific work flows assesses and tracks activities that are initiated and carried out by humans, such as healthcare or social services workers (i.e. follow up after a patient at high risk for suicide after a missed appointment), these attributes and objective observations made by the system on each patient's care as carried out by human actors can be input into the inventive systems predictive analytics and proprietary scoring algorithms. Scores generated from these proprietary algorithms can, of course be used in predicting the risk for suicide, but also can be used to provide aggregate, subgroup and individual performance data (of how well the suicide prevention team stakeholders are carrying out their responsibilities) over particular date ranges and at various snapshots in time enabling healthcare provider organizations, managers, and facility leaders to monitor processes in real time and over time and improve performance/maximize the effectiveness of their efforts to prevent a potential suicide. This data is also used as inputs into the inventive system's proprietary facility "Suicide Prevention Readiness Score (SPR Score or SPRS)." Those provider organizations that subscribe to the system's benchmarking service, can view their SPRS scores relative to similar (deidentified) peer organizations as a means of assessing their relative performance. This real time analytics, scorecard, and dashboard data can be accessed via the system's native or web browser based client applications via desktop computers or workstations or mobile devices. The system is also configured to provide large screen displays that can be mounted on the wall in areas used by healthcare and social services worker teams, analysts, managers, and administrators of healthcare provider organizations. Displays can be configured to show only de-identified data and/or aggregate data or if in a restricted area, more granular data to support the workflows described herein.

The system's client applications utilize the system's server side application programming interface for secure communications and data exchange. The system is capable of exposing its application programming interface to third party developers enabling them to develop additional client applications that leverage the inventive system's predictive analytics tools and functionality. The system provides a plurality of APIs (for example, but not limited to, messaging based, web sockets, HTTP based, Remote Procedure Call or Windows Presentation Foundation based, etc.) and some of which employ an interoperability standard such as REST, RESTful or RESTlike or Fast Healthcare Interoperability Resources (FHIR), to name a few.

The client applications provide a "patient panel" or list of patients with particular aspects of their care that is being managed at a given facility. One example for how these client applications are used is, to track certain milestones and events and to ensure compliance with the collection of certain clinical and administrative documentation that is required as part of the suicide prevention clinical pathway. The graphical user interface provides situational awareness into issues or situations that may require intervention by a field healthcare worker or case manager; this includes, to provide one example, alerts about certain documentation that is due soon, due, or past due/missing. This client application that is a part of the system is a tool that organizations such as payors or large provider organizations, such as the Veterans Health Administration can use to improve compliance with particular work flows and ensure collection of particular clinical and administrative documentation necessary for compliance with contracts with community providers, for example those for the provision of "non-VA care." Additional use cases for the system's client applications (and API calls that can be used by third party developers) are those in which field healthcare workers such as the case managers supervising/monitoring/tracking outsourced care for patients at risk for suicide that are receiving services in the community to capture data that is part of particular clinical pathways and administrative milestones and process checks.

The client applications and APIs can also be used by field healthcare workers such as case managers to capture (i.e. author or dictate) clinical documentation and submit said documentation to the referring entities electronic health record for the patient. Furthermore the video sensor on the client devices and or API calls that are used by third party developers that integrate other client devices into the system can be used to share clinical and administrative documentation (i.e. as another means of healthcare information exchange) that is needed clinically or required to be submitted contractually as a part of oversight, monitoring and assessment of the services provided by contracted community provider organizations. Where applicable, this data is yet another input that the system can be configured to input into its predictive analytics, one example of which would be data inputs into care plans and clinical pathways that have been configured in the system.

The system provides a user interface in one of its client applications that allows suicide prevention coordinators and other healthcare workers and provider organization managers and leaders to manage, monitor and assess both clinical and administrative aspects of the patient's care (individual patients or patients in aggregate) at their facility and at remote facilities that may be solely or jointly caring for the patient, for example in the case of "non-VA care." In addition to healthcare workers, other stakeholders such a patient centered medical homes, accountable care organizations, payor organizations, etc. can leverage the platform to manage and monitor the patient's care progression and the real-time analytics and data visualization tools therein; both individual and aggregate views are provided. Examples of this activity includes, but is not limited to, appointment scheduling, whether the patient has or has not showed up for a given visit, consult requests and whether the consult request has been fulfilled/completed, tracking the providers, mental health, social services, and healthcare workers involved in the patient's care collectively and their charting and documentation on the patient including metadata about the charting as previously described and the content of the charting itself, unplanned visits such as emergency room visits, hospital admissions, ambulance transportation records, law enforcement data, and clinical documentation and claims submitted for payment for rendered services at any facility.

Using the system's proprietary technology enabled work flows provider organizations and payors to monitor the status and progress of patients at risk for suicide across a potentially heterogeneous mix of healthcare provider organizations, mental and social services providers, home health services providers, community organizations such as the Salvation Army, and other services providers. The system utilizes data collected via this technology enabled work flow as an input to its proprietary machine learning predictive analytics. The system further leverages this data it collects organically over time as inputs to its proprietary scoring algorithms that rate healthcare provider organizations and services providers on the care they provide to patients at risk for suicide, as described elsewhere herein.

Furthermore the system is able to use proprietary analytics to make recommendations at particular junctures in the patient's care across the local and remote healthcare provider organizations; for example, should a given patient, for example, but not limited to, one at high risk for suicide, need a referral for mental health services locally or in the community or at another facility, be it psychological services, psychiatry services, group counseling services, home health services, etc., the system can examine attributes of the patient in need of referral and leverage its proprietary trained models to provide a ranked list of potential matches for the patient that provide the services in need and that optimize the prioritized input parameters (leveraging data known by the system about similar patients and the process metric data and outcomes from the services they received at various available local or remote providers/provider organizations).

The system can be configured by the end user to maximize, weight or prioritize particular factors in making match recommendations including attributes such as, how soon the patient needs to be seen, how important it is that the patient be seen by or before the requested date, the distance from the patient's residence, accessibility via public transportation, patient preference etc. or particular outcomes or process metrics known by the system which it learns over time about the available services providers (for example, from clinical documentation and claims received, or not received) used by previous patients the system has seen (for example, data such as, but not limited to, current patient/case load, no show rates, appointment cancellations, suicide rate of previously referred patients, timeliness of services rendered and frequency of complete and high quality documentation of the services rendered, findings, assessments and interpretations, etc.).

Furthermore, one of the system's client applications provides patient panel functionality to aid the suicide prevention and other healthcare workers in managing a proprietary technology enabled clinical and administrative work flow tailored to the use case where patients receive care across a potentially heterogeneous set of local or remote (i.e. in the community) provider organizations involved in the provision of healthcare, mental health, and other services to patients at high risk for suicide. A portion of this use case was described earlier herein.

The system makes available configuration settings that allow the entry of business rules relating to particular suicide prevention clinical pathways and related key performance indicators (KPIs). Care provided to patients at high risk for suicide is assessed against the configured clinical pathways and KPI performance is calculated. This output of these analytics and the input data is used by the system in its predictive analytics and by its recommendation engine described above. Also leveraging its proprietary technology enabled work flow and business rules derived from configured care plans or clinical pathways the system provides proprietary scoring of remote (i.e. community based) services providers to which a given entity using the system refers patients. Via its data visualization, dashboard and score card user interfaces in its client applications, the system provides real time and historical analytics depicting the performance of local services providers (i.e. in house), remote (i.e. community based) services providers and other providers to which a given entity using the system refers patients for care. The data visualizations can highlight trends at a moment in time and over time relating the system's proprietary scoring algorithms and related to performance against related clinical guidelines, business rules, and clinical pathways bringing clarity to the assessment of relative performance versus benchmarks, peer provider organizations, etc.

Healthcare provider organizations that utilize the system can implement it as an enterprise system or use a multi-tenant deployment of the system. Entities using the system can choose to use models that are continuously trained only using data that relates to patients whose care they manage locally or in conjunction with other entities or organizations to train the predictive analytics machine learning models. However, the system is capable of providing access to machine learning models that have and are being trained on an ongoing basis from data from one or a plurality of healthcare provider organizations. Thus, the system can provide access to potentially more accurate predicative analytics via its ability to enable entities using the platform to opt into shared training of the system's models; in other words, a given entity, even in an enterprise deployment, can opt into sharing data securely to a server deployment of the system that receives data from a plurality of the system's deployments that trains models, and then makes said trained models available to entities that have opted into this service.

Entities deploying the system for this purpose can then use the system's notification micro service to obtain real time situational awareness and alerts about individuals that may be at risk for suicide and potentially in need of intervention, outreach and/or healthcare and mental health services. The entities deploying the system are able to establish predefined business rules in regards to particular individuals that should be notified via the notification micro service in particular scenarios (i.e. particular predicted outcomes); an example may be a case manager, social worker or other healthcare worker employed by the entity with a job responsibility for fielding such alerts and determining what action needs to be taken or automated routing of notifications from the inventive system to a call center for an outreach call/check by a an individual with specific training in suicide prevention. In addition, if the individuals being assessed for potential risk of committing suicide have had opted into potential notification of particular authorized individuals, for example family members, spouses, healthcare providers, case managers, social workers, or any other individuals, the system can be configured to request specific actions by a plurality of said individuals. To provide an example, the system could be configured to ask particular individuals to check on (call or visit) the individual and asked to report back specific information via the system's client application. This can be as simple as: "Was able to contact XYZ" and/or "I have spoken to XYZ and they are okay" or "I was not able to contact XYZ after N attempt(s)." This interaction would be via the patient facing (or family or care giver facing) client applications of the system previously described herein.

The DCE or server device can determine the patient's risk for suicide based upon the data enumerated above and technology enabled work flows described herein utilizing algorithms developed leveraging machine learning techniques including neural networks, support vector machines, genetic programming, genetic algorithms, Bayesian statistics, decision trees, case based reasoning, information fuzzy networks, particle swarm optimization, simulated annealing, among others, that allow for complex pattern recognition, in some cases, leveraging pre-existing or previously collected "training" data, in addition to any newly acquired data, to predict an outcome, namely, in this use case, the probability that a patient is at risk or will attempt to take their life or changes in the risk profile or "risk signature" over time.

Using the above described methods, the system leverages proprietary models that are trained, for example, using supervised machine learning and the above enumerated data from cases known to and known not to have committed suicide, and uses the trained models to then make predictions on new patients or cases the system has not seen previously. The system is designed to be configurable such that it can evolve and consume new data types/sets as inputs to its predictive technologies. The system's models are capable of ongoing learning over time (continuous training of its models) and is thereby capable of learning from new data in real time allowing for maintenance of and potentially improvement in the inventive systems predictive capabilities, particularly as behaviors evolve and new data sources are introduced.

As mentioned above, the server device (or DCE) can utilize machine learning algorithms to predict events related to, risk of suicide or changes therein. A trained model can be used to determine whether a patient that has been flagged to be at risk for suicide (to address one use case of the system described herein) has had a change (for example a worsening) in the predicted risk of suicide. For example, using a simple, human understandable example, if a patient did not show up to an appointment and was not able to be reached subsequently by a healthcare worker that followed up as determined by documentation, the system ingests and analyzes, the trained model would be used by the system after registering each event to assess whether the pattern of events in the context of other data the system has access leads to a significant increase in the individuals predicted risk for suicide. To provide one example of how this is done, the server device can train a Neural Network Model (NNM) to generate an output value to make this prediction.

First Embodiment

Referring to FIGS. 6-13, a first embodiment will be discussed by exemplary cases in which the DCE 102 receives medical data from the RFID tag. In the case shown in FIG. 8, the DCE 102 is located at medical facility room 900. A Patient ID badge 70 including an RFID tag (passive or active) 910 is worn by a patient 60. The DCE 102 establishes communication with the RFID tag 910. Particularly, the DCE 102 can periodically generate a broadcast message, and receive a registration message including identification data from the RFID tag 910 in reply to the broadcast message. Alternatively, the RFID tag 910 can self-initiate sending of the registration message periodically or in response to another external trigger.

Figure 9:
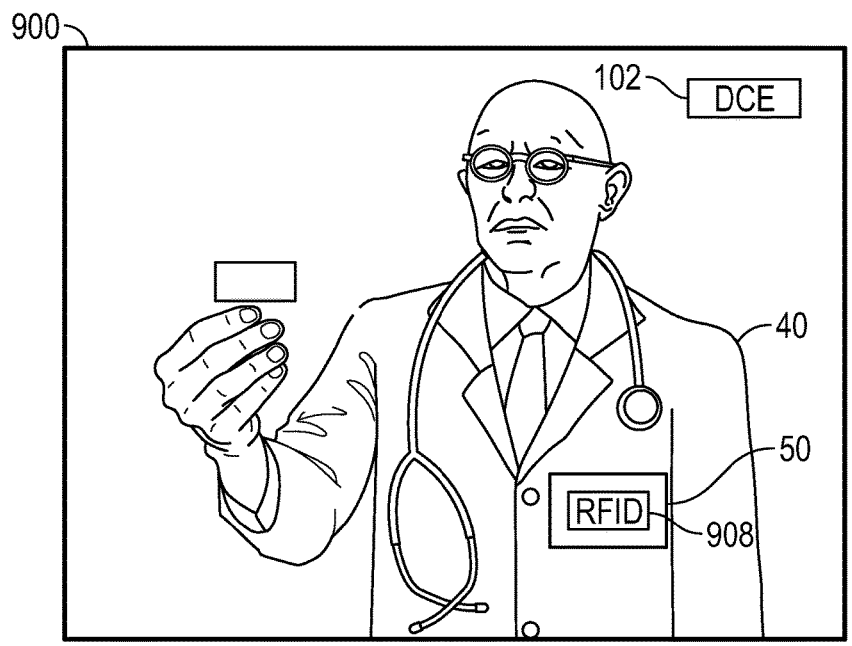
FIG. 9 is an illustration of an exemplary medical professional wearing an identification badge with a RFID tag.

If the RFID chip 910 is a passive type, it can send the data while receiving power from the DCE 102. In this case, the event would be the patient 60 showing up for a scheduled medical appointment as indicated by the patient 60 being in the medical facility room 900. In FIG. 9, the doctor 40 is wearing a medical professional ID badge 50 including an RFID tag 908. The DCE 102 communicates and receives data from the RFID tag 908 when the doctor 40 enters the medical facility room 900. The RFID tag 908 sends a message including identification data indicative of a second event to the DCE 102. In this case, the second event is that the patient 60 is being seen by the doctor 40. When the RFID tag 908 in the medical professional ID badge 50 is no longer in proximity to RFID tag 910 in the patient ID badge 70, the RFID tag 910 sends a message including data indicative that the medical appointment has concluded. The RFID tag can include a sensor for detecting near presence of another RFID chip. The DCE 102 can then send one or more messages indicative of the events to be sent to the server device 114 via the network connection. This exemplary embodiment illustrates how the inventive system gathers RFID data as a patient event for data input into the NNM.

Figure 6:
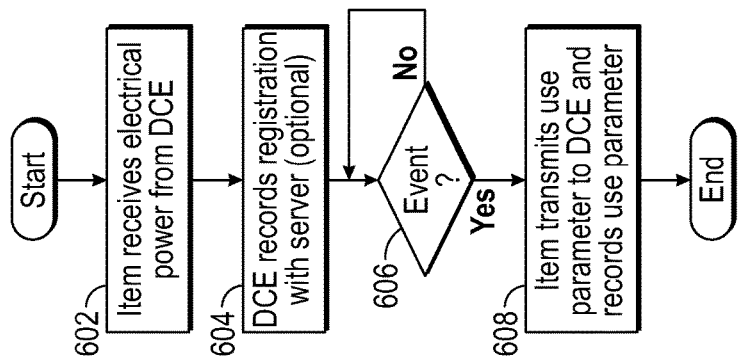
Figure 8:
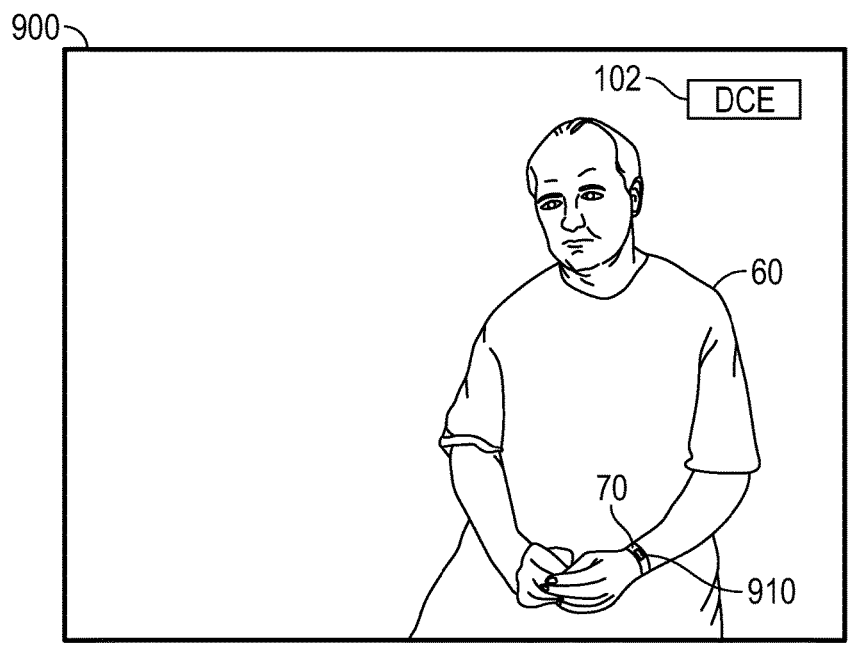
FIG. 8 is an illustration of an exemplary patient wearing a patient identification band with a RFID tag.

Referring to FIG. 6, the operations of the RFID tag and the DCE in a simple scenario will be discussed. At 602 a passive-type RFID chip receives electrical power wirelessly from the DCE. The wireless power can be sent along with a regular general broadcast message from the DCE or an interrogation request. Of course, if the RFID chip is active-type, this step can be omitted. At 604, the RFID tag sends registration information to the DCE, which records it in its memory. Particularly, the registration information can include the identification of the RFID tag. At 606, if the RFID tag and/or the DCE determines that an event has occurred, at 608 the RFID tag sends use parameters associated with the event to the DCE. The DCE records the usage parameters in its own memory or immediately transmits the information to the server to be stored in the medical item database.

Referring to FIG. 6, the operations of the RFID chip and the DCE in a more complex scenario in which a medical professional such as a doctor meets with a patient will be discussed. At 702, the doctor 40 wearing an identification such as a badge including an RFID chip (active or passive-type) 908 enters a room 900 within the communication area of the DCE 102 and the RFID tag 908 registers with the DCE 102. A patient 60 with a patient identification 70 including another RFID tag 910 which has already registered with the DCE 102 is already in the room 900. At 704, the DCE 102 records a first event indicative of the patient 60 and the doctor 40 being in the same room and the start time. At 706, the DCE 102 generates a message representative of this first event to be transmitted to the server. At 708, the doctor 40 wearing the identification 50 including the RFID tag 908 leaves the room 900 and disconnects from the DCE 102. At 710, the DCE 102 records the time the RFID tags disconnected as the end time of the first event and generates a message representative of the end time of the first event to be transmitted to the server.

Figure 12:
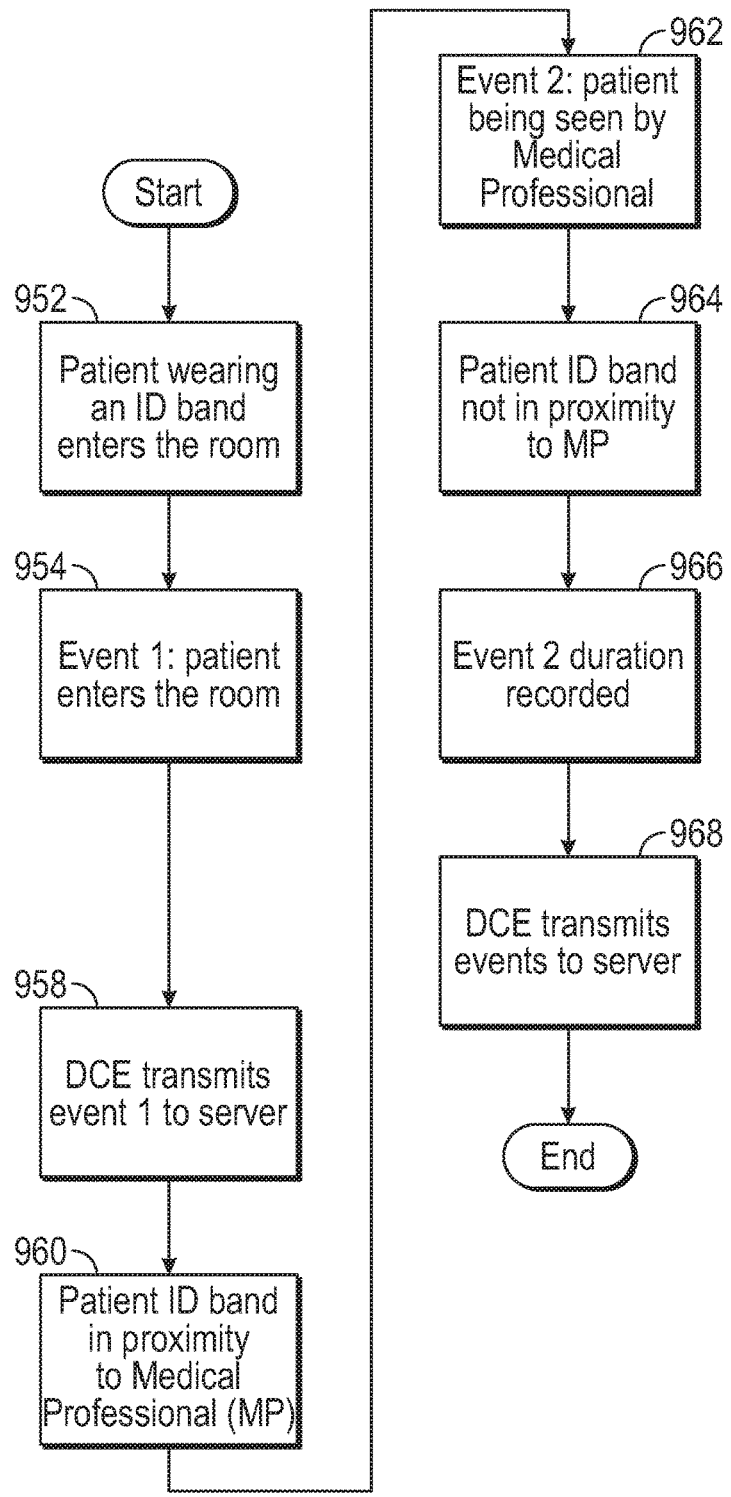
FIG. 12 is a flow diagram illustrating exemplary operations of the system.

Referring to FIG. 12, operations of the system for an exemplary patient event in which a patient arrives to a medical appointment will be discussed. Although the example is different, reference numerals from FIGS. 8-9 will be used again for ease of understanding and brevity. At 952, the patient 60 wearing the patient ID band 70 including the RFID tag 910 enters the room 900. At 954, the DCE 102 establishes communication with the RFID tag 910 and records the location and patient identification as "Event 1". At 958, the DCE 102 transmits a message indicative of "Event 1" to the server. At 960, it is detected that the patient ID band 70 is in proximity to the doctor's ID badge 50. For example, the DCE 102 can receive registration messages from both the RFID tag associated with the doctor's ID badge 50 and the RFID tag 910 of the patient 60 and thereby conclude that the doctor and patient are in the same room. Alternatively, if one of the RFID tags is an active-type RFID tag while the other is a passive-type RFID tag, if the passive-type is activated by power from the active-type RFID tag, one of these tags can transmit a message to the DCE indicative of this relationship. Further, one of the RFID tags can include a sensor for detecting when another type of RFID tag is within a predetermined distance. At 962, the DCE 102 records a patient event indicative of the patient 60 and doctor 40 being in the same room and the start time. At 964, it is detected that the patient ID band 70 is no longer in proximity to the doctor 40, similar to the detection method of 960. At 966, the DCE 102 records the duration of the patient event as "Event 2". At 968, the DCE 102 transmits the patient event Event 2 to the server 114. The RFID chips can detect separation from another RFID chip or being within a predetermined distance from another RFID chip by the sensor group. Alternatively, the detection can be performed by ambient radio frequency communication techniques which can detect proximity up to, for example, 70 cm by backscattering. Further, the detection can be performed at the DCE end by, for example, measuring the RSS of the RF signal received from the chips.

Figure 13:
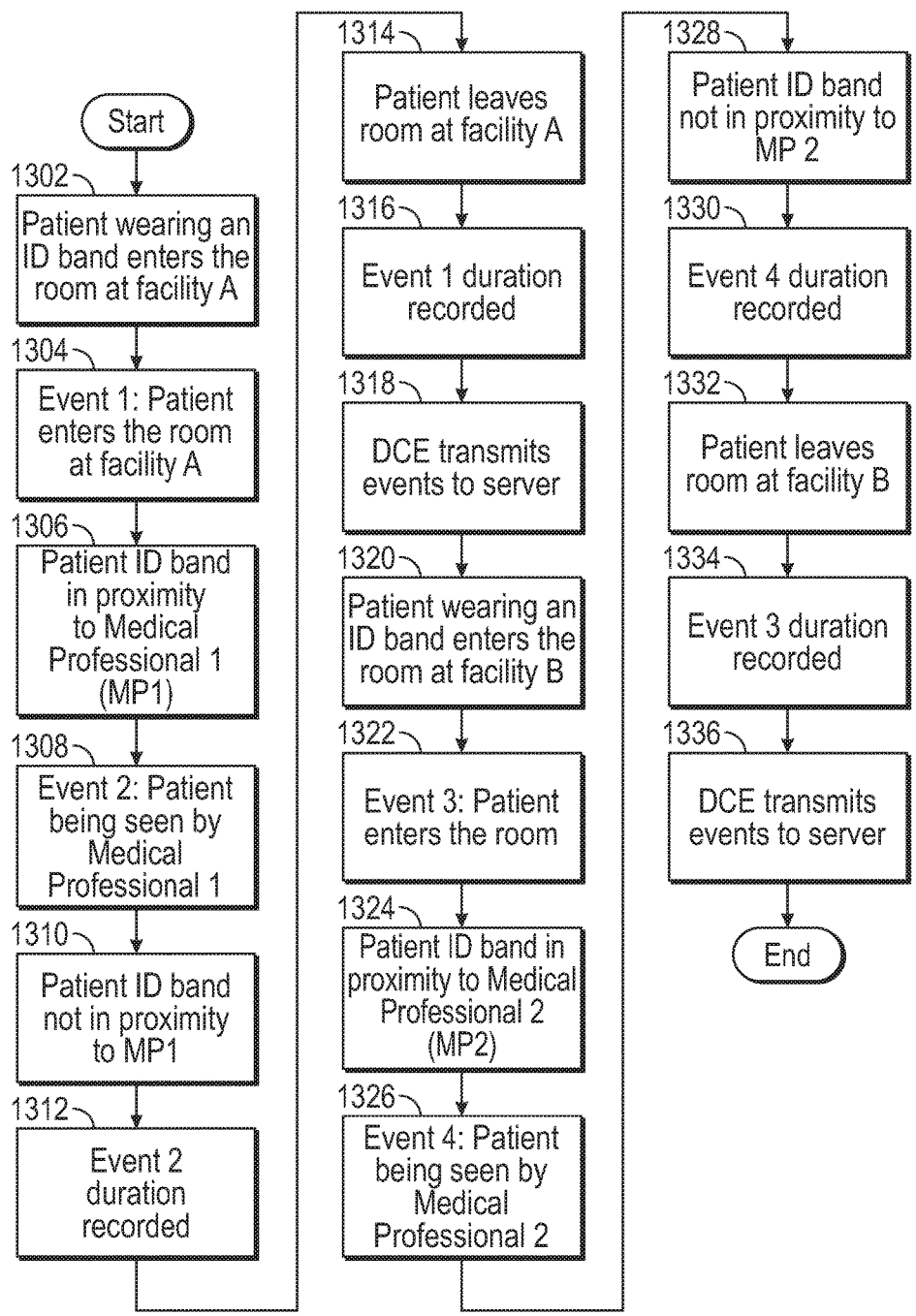
FIG. 13 is a flow diagram illustrating exemplary operations of the system in an example in which a patient is treated at two unaffiliated facilities.

Referring to FIG. 13, operations of the system during an exemplary scenario in which a patient receives care at multiple facilities will be discussed. In this exemplary scenario, the data collected could be whether the patient went to two separate appointments with two different doctors at two unaffiliated healthcare providers. At 1302, the patient wearing a patient ID band including an RFID tag enters a room at facility A having a DCE disposed, for example, on the ceiling to define a coverage area. The RFID tag sends a registration message identifying itself to the DCE in response to a polling request or broadcast message. At 1304, the DCE registers the patient associated with the RFID tag in the room as "Event 1". At 1306, the patient becomes in proximity to a medical professional (MP1). It is detected that the RFID tag in the patient ID band detects is in proximity to the RFID chip associated with the first doctor's ID badge by one of the RFID tags, a sensor, and/or the DCE similarly to as discussed with respect to step 960 in FIG. 9. At 1308, the DCE records that the patient is being seen by MP1 based upon the detection as "Event 2". At 1310, the patient ID band is no longer in proximity to the MP1. This can also be detected similarly to as discussed with respect to step 960. At 1312, the DCE records the duration of Event 2 based upon the time from which the RFID tags were in proximity. At 1314, the patient leaves the room at facility A. This can be detected by, for example, the end of communication between the DCE and the RFID tag associated with the patient or based upon location information received from the RFID tag. At 1316, the DCE records the duration of Event 2 based upon when the patient left the room at facility A. At 1318, the DCE transmits the first and second events to the server.

At 1320, the patient wearing the patient ID band including the RFID tag enters a room at facility B having a DCE disposed, for example, on the ceiling to define a coverage area. The RFID tag sends a registration message identifying itself to the DCE in response to a polling request or broadcast message.

At 1322, the DCE registers the patient associated with the RFID tag in the room as "Event 3". At 1324, the patient becomes in proximity to a medical professional (MP2). It is detected that the RFID tag in the patient ID band detects is in proximity to the RFID chip associated with the second doctor's ID badge similarly to as discussed with respect to step 960 in FIG. 12. At 1326, the DCE records that the patient is being seen by MP2 based upon the detection as "Event 4". At 1328, the patient ID band is no longer in proximity to the MP2. This can also be detected similarly to as discussed with respect to step 960. At 1330, the DCE records the duration of Event 4 based upon the time from which the RFID tags were in proximity. At 1332 the patient leaves the room at facility B. This can be detected by, for example, the end of communication between the DCE and the RFID tag associated with the patient or based upon location information received from the RFID tag. At 1334, the DCE records the duration of Event 3 based upon when the patient left the room at facility A. At 1336, the DCE transmits the third and fourth events to the server.

In the above example, the DCE can be separate DCE's at facility A and facility B. Both DCE can register the two events as first and second events, but the server can recognize these as four different events upon receiving the messages indicative of the events from the respective DCE.

Second Embodiment

Referring to FIGS. 14-36, a second embodiment will be discussed in which the server device 114 utilizes a trained model to make predictions regarding events.

Creating a Trained Neural Network Model to Predict an Outcome

Figure 14:
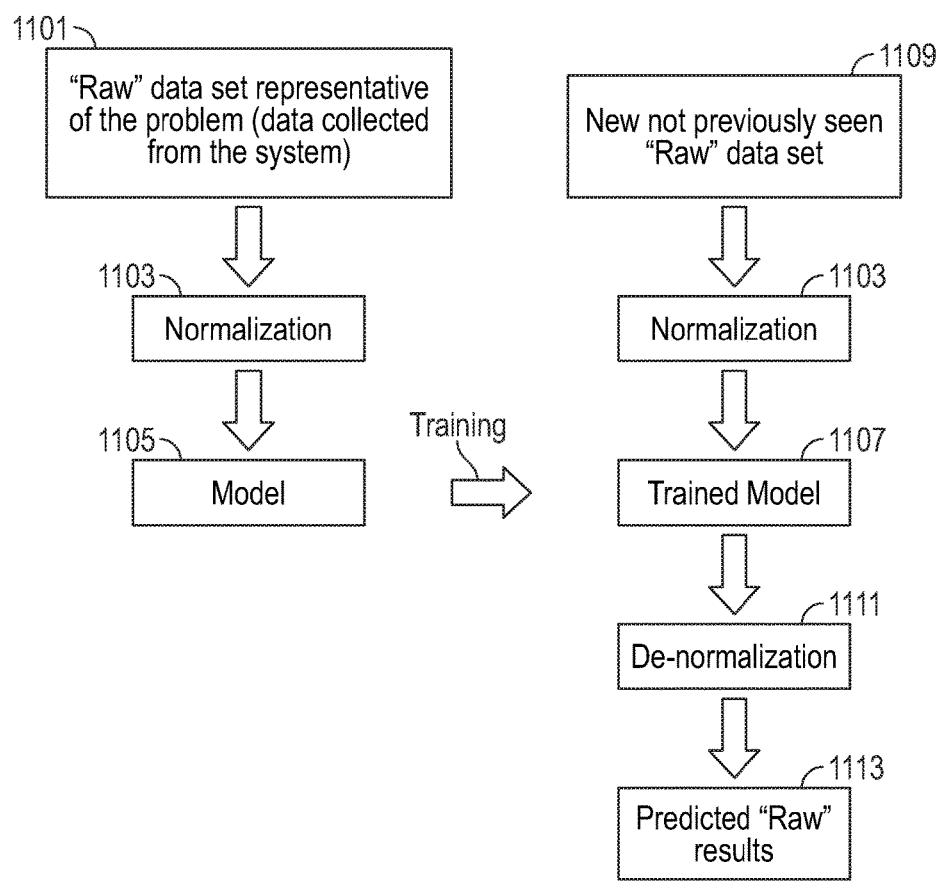
FIG. 14 is a block diagram illustrating high level operations for creating a trained neural network model (NNM) according to an embodiment.

The server device 2014 stores a trained neural network model which is used to predict an outcome of a clinical patient event. A representation of the process for creating, training and using the trained model is shown in FIG. 14. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 15, the raw data 1101 and new data 1109 include sets of data [1, 2 . . . N] with known outcomes and properties of each of the data. For example, the data can be past patient events with known suicide outcomes. The properties of the data can be suicide attributes.

The model 1105 is trained by an iterative machine learning algorithm. After initial deployment, the server 2014 will also continuously collect data from a variety of sources along with actual related healthcare system clinical and operational outcomes; this data can subsequently be used as training data. As such, the server 2014 is able to continuously learn and improve its ability to predict the outcomes of interest. In addition, the knowledge of the system can continue to evolve in the event the system dynamics change.

There is a relationship between the multitude of attribute data the system collects about a suicidal behavior and the outcome in question. Exemplary suicide attributes the server 2014 collects about a suicide risk can be used include, for example, marital status change and loss of employment. However, there is no one specific mathematical relationship or equation that describes the relationship between attributes of the suicide risk and the outcome of interest. However, because of the server's machine learning capabilities it has the ability to "learn" or be trained from pre-existing data and from the data it collects prospectively. Said another way, the server 2114 "learns" from experience.

Data Set Encoding, Normalization and De-Normalization

Neural network models only use numerical double values for training and processing. Thus any nominal categorical data fields that are a part of raw data that will ultimately be used by models in the system are first encoded to numerical values and "raw" numerical data in many cases by a pre-processing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

An example of one of the independent predictors (input x-data) or discharge attributes that can be utilized by the system is the number of medications a given patient is prescribed at the time of discharge. Suppose a patient has 19 discharge medications and that this "raw data" value needs to be normalized to a −1 to 1 normalization range. If the actual range of the possible number of discharge medications is 0 to 50, for example, then to normalize this input x-data, the system's continuous or numeric normalization process would carry out normalization calculations similar to those illustrated herein. Initially, the value can be plotted on an actual range as shown in FIG. 16. Then a normalization calculation can be carried out as shown below:

$$\{[(19-0.0)*(1.0-(-1.0))]/(50.0-0.0)\}+(-1.0)=-0.24$$

Referring to FIG. 17, equivalent value plotted on a normalization scale is shown.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 18. For example, one of the attributes that may be used is the medical specialty. In this case, at 1902, the attributes have three medical specialties: hospital medicine, psychiatric care and community organizations. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is psychiatric care {0.0, 0.0, 1.0} but the ideal (real) value is actually psychiatric care {0.0, 1.0, 0.0} as shown at 1904, it is apparent that there is only error in two parts. Said another way, if the predicted and the ideal (real) values are compared, the first value is 0.0 in both (i.e. is correct), while the other two values are both wrong. This is unequal distribution of errors.

Due to this shortcoming of one-of-N encoding, particularly in instances when there are more than two nominal categories, the server can employ equilateral encoding (one-of-(N−1) encoding shown in FIG. 19 or one-of-(C−1) dummy encoding for encoding nominal categorical data. When equilateral encoding is used fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$\text{distance} = \sqrt{\frac{(i_1-a_1)^2+(i_2-a_2)^2+\ldots+(i_n-a_n)^2}{n}}$$

Where the variables represent the following:
i=ideal (real) output value
a=actual (predicted) output value
n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
=$((0.5-0.933)^2+(1.0-0.25)^2)^{1/2}$
=$(-0.433^2+0.75^2)^{1/2}$
=$(0.187489+0.5625)^{1/2}$
=$(0.749989)^{1/2}$ =0.8660
Ideal: {0.06698, 0.25}
Actual: {0.5, 1}
Euclidean Distance:
=$((0.06698-0.5)^2+(0.25-1)^2)^{1/2}$
=$(-0.43302^2+(-0.75^2))^{1/2}$
=$(0.1875063204+0.5625)^{1/2}$
=$(0.7500063204)^{1/2}$
=0.8660

Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others. While the exemplary embodiments herein do not detail every machine learning approach employed by the system to solve the technical problem, this should not be construed as an omission of these capabilities or approaches which the system can and in some case does leverage to solve the technical problem.

There are three primary categories of machine learning tasks: classification, regression and clustering tasks.

Classification

Figure 20A:
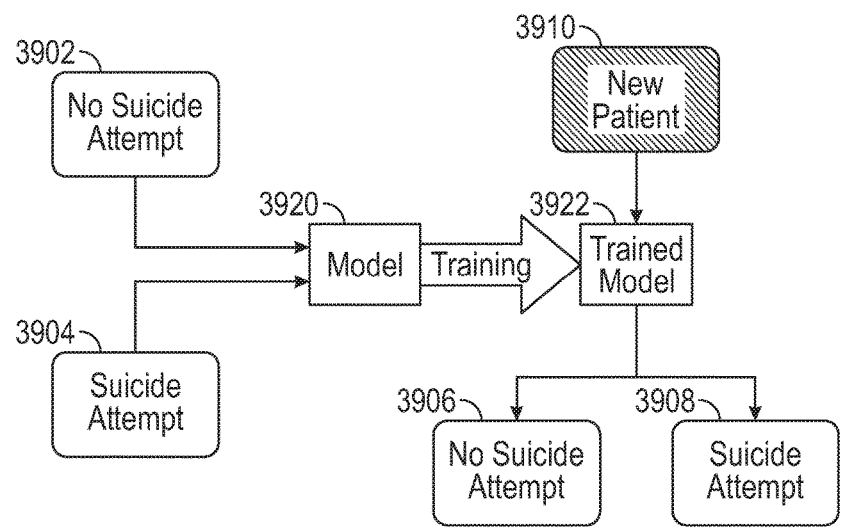
FIGS. 20A-20C are illustrations of a case in which the model is used to categorize the suicide risk of a plurality of patient events.
Figure 20B:
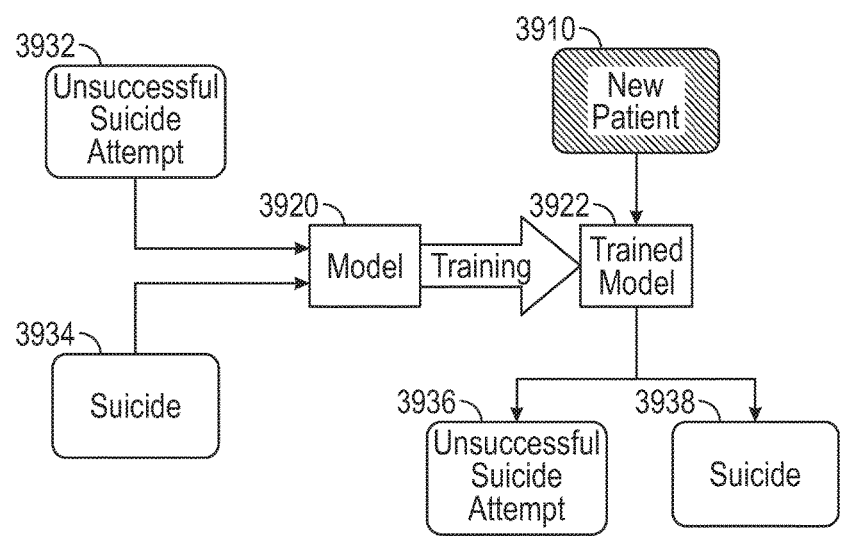
Figure 20C:
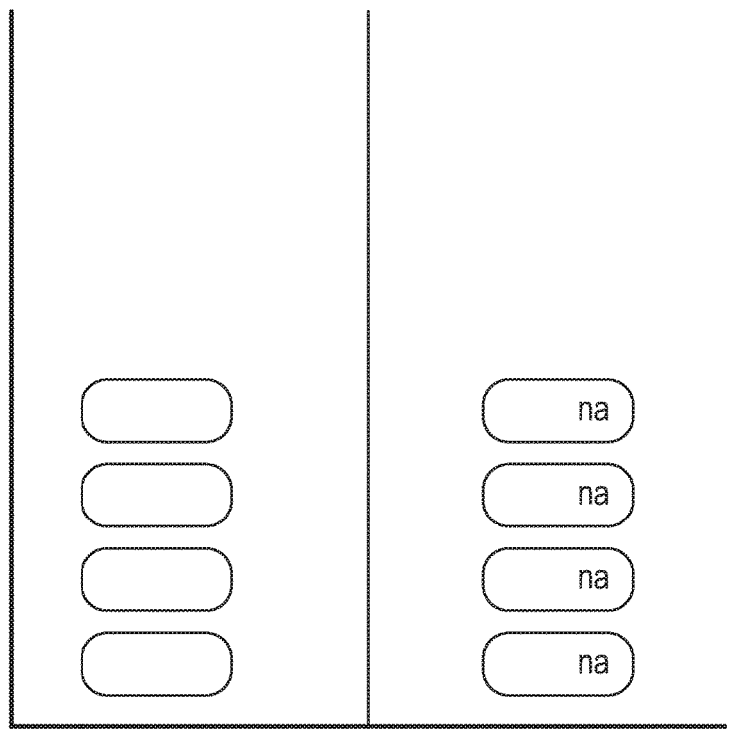

Referring to FIG. 20A-20C, a classification task for predicting a suicide risk is shown. The machine learning task entails a two-step supervised learning process which utilizes both input and output data in the model training process. Model construction is done using a representative training data set and the model 3920, once trained 3922 is used for classifying new or unseen cases. The inputs are collected suicide risk data attributes/properties such as no suicide attempt 3902, suicide attempt 3904, unsuccessful suicide attempt 3932 and suicide 3934. The output for a new patient 3910 will be the predicted categorical risk for a suicide attempt 3908 or no suicide attempt 3906 as one example or a suicide 3938 or unsuccessful suicide attempt 3936 as another example.

Regression

Figure 21:
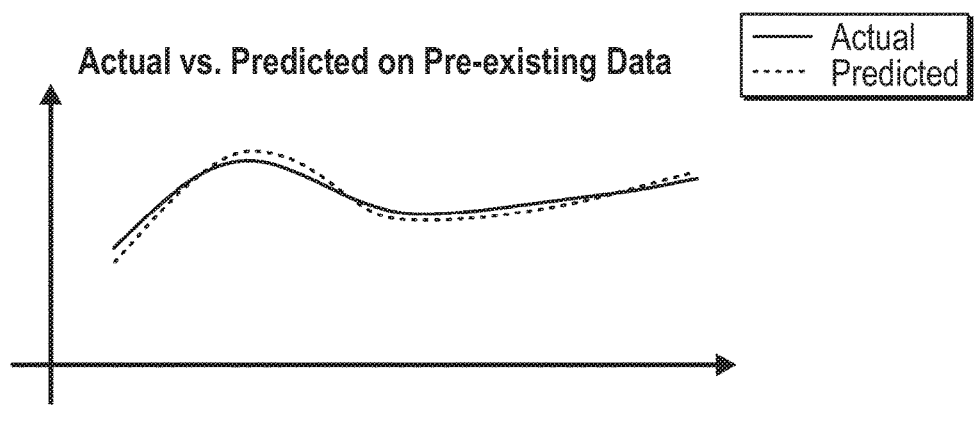
FIG. 21 is an illustration of exemplary regression tasks performed by the client device.
Figure 21:
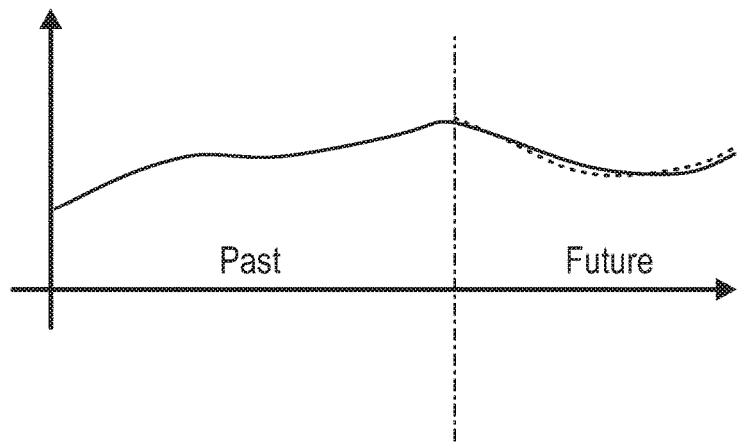

Referring to FIG. 21, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of discharge delay (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 2014 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boosts model performance and efficiency for some tasks.

Another exemplary task, for which the server 2014 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 22:
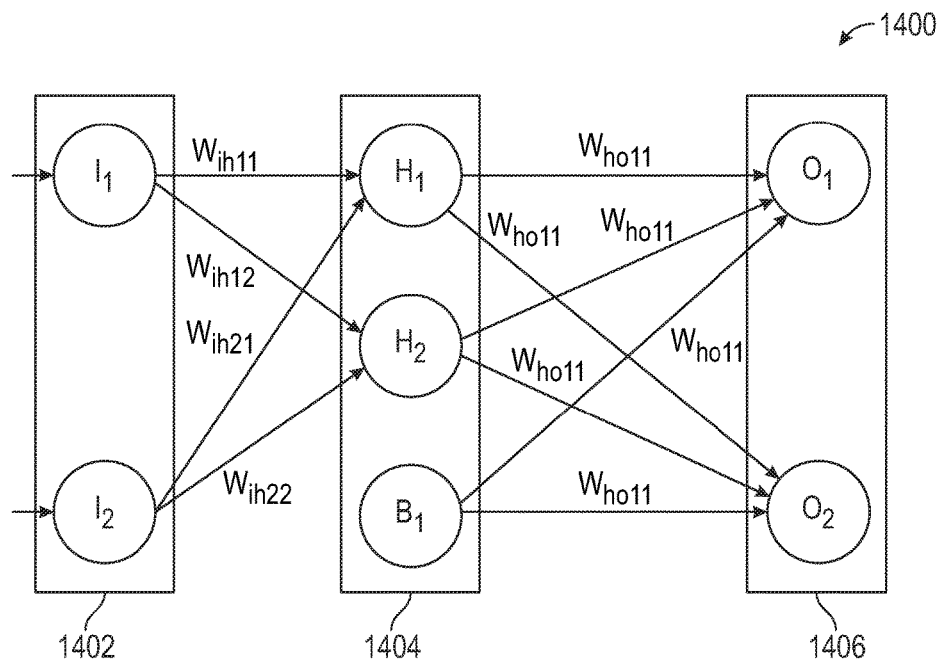
FIG. 22 is an illustration of an exemplary simple feed forward NNM.

Referring to FIG. 22, the backend devices can use a neural network model (NNM) 1400. The NNM 1400 includes an input layer 1401, a hidden layer 1404 and an output layer 1406. The input layer 1401 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons ($B_1$) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $w_{ih\ 12}$. The $w_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus the notation $w_{ih\ 12}$ not only denotes the neurons that are connected or involved but also the direction of the connection.

Figure 23:
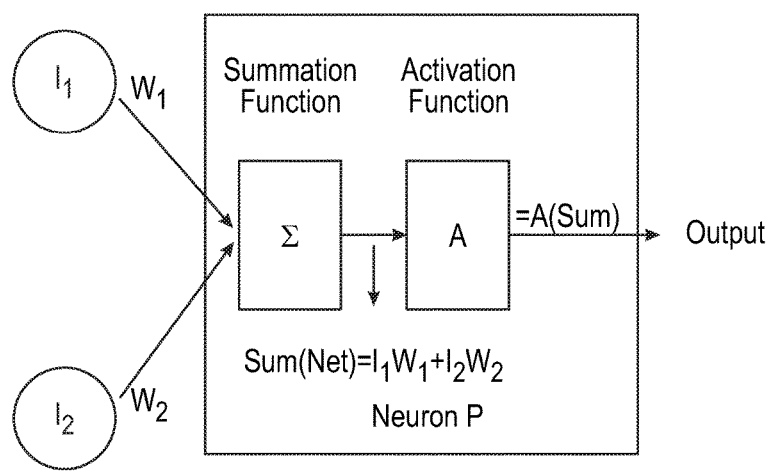
FIG. 23 is an illustration of an exemplary neuron of the NNM.

As shown in FIG. 23, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The Sigmoid Function $$f(x) = \frac{1}{1+e^{-x}}$$

Figure 24A:
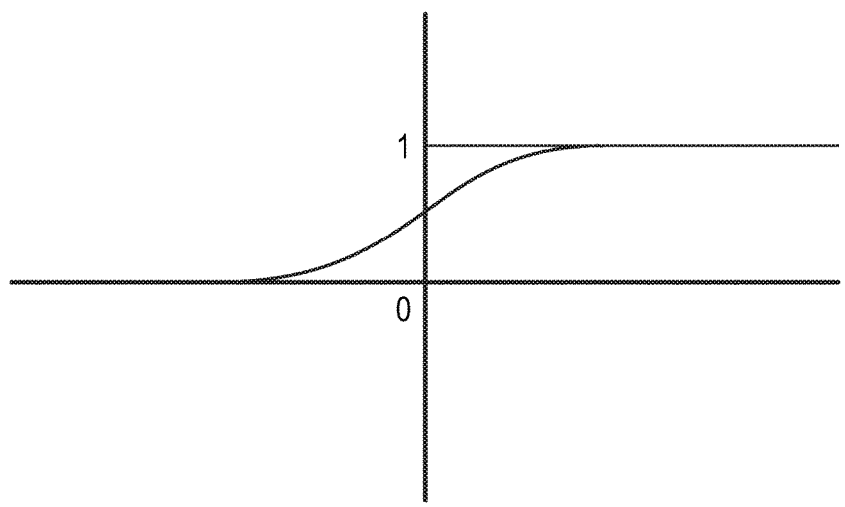
FIGS. 24A-24C are illustrations of exemplary activation functions for the neurons of the NNM.

As shown in FIG. 24A, a characteristic of the sigmoid function is that for all values on the x axis, the function output value (y axis) will lie between 0 and 1. The sigmoid function is used in instances where only positive outputs are expected.

The Hyperbolic Tangent Function $$f(x) = \frac{e^{2x}-1}{e^{2x}+1}$$

Figure 24B:
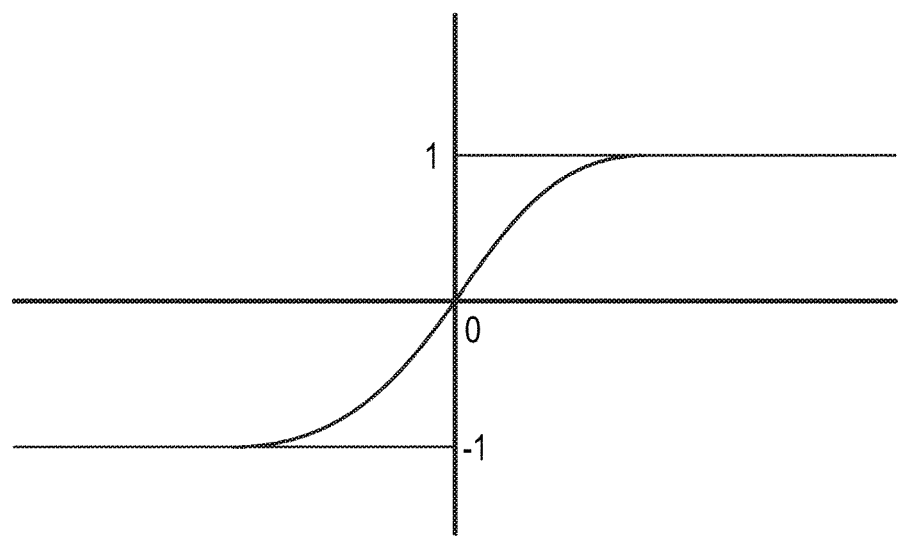

As shown in FIG. 24B, a characteristic of the hyperbolic tangent function is that for all values on the x axis, the function output (y axis) will lie between −1 and 1. The hyperbolic tangent function is used by the system in instances when both positive and negative outputs are expected.

The Linear Function $$f(x)=x$$

Figure 24C:
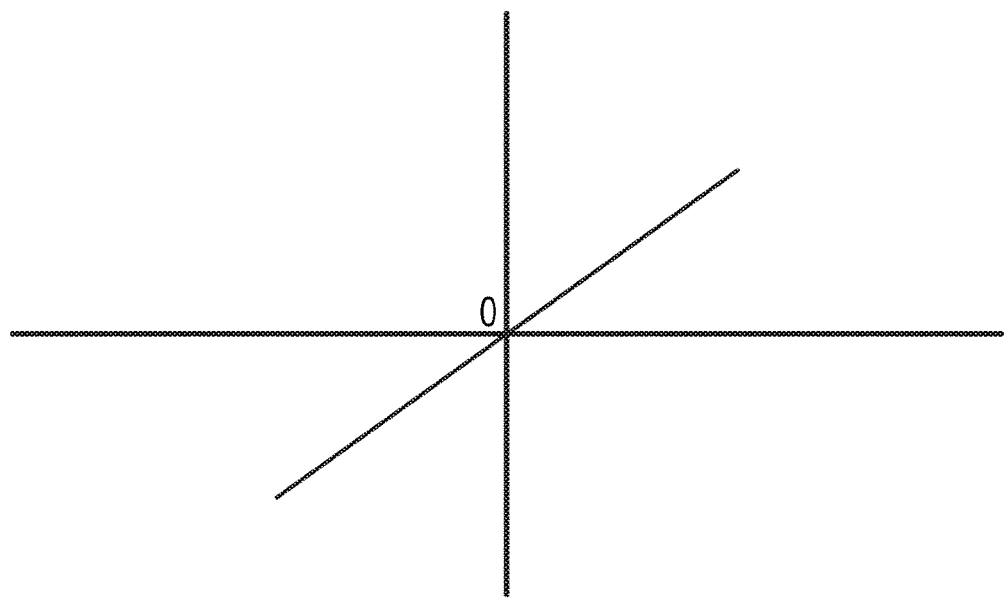

As shown in FIG. 24C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 2014 employs a plurality of activation functions to accomplish its objectives.

Figure 25:
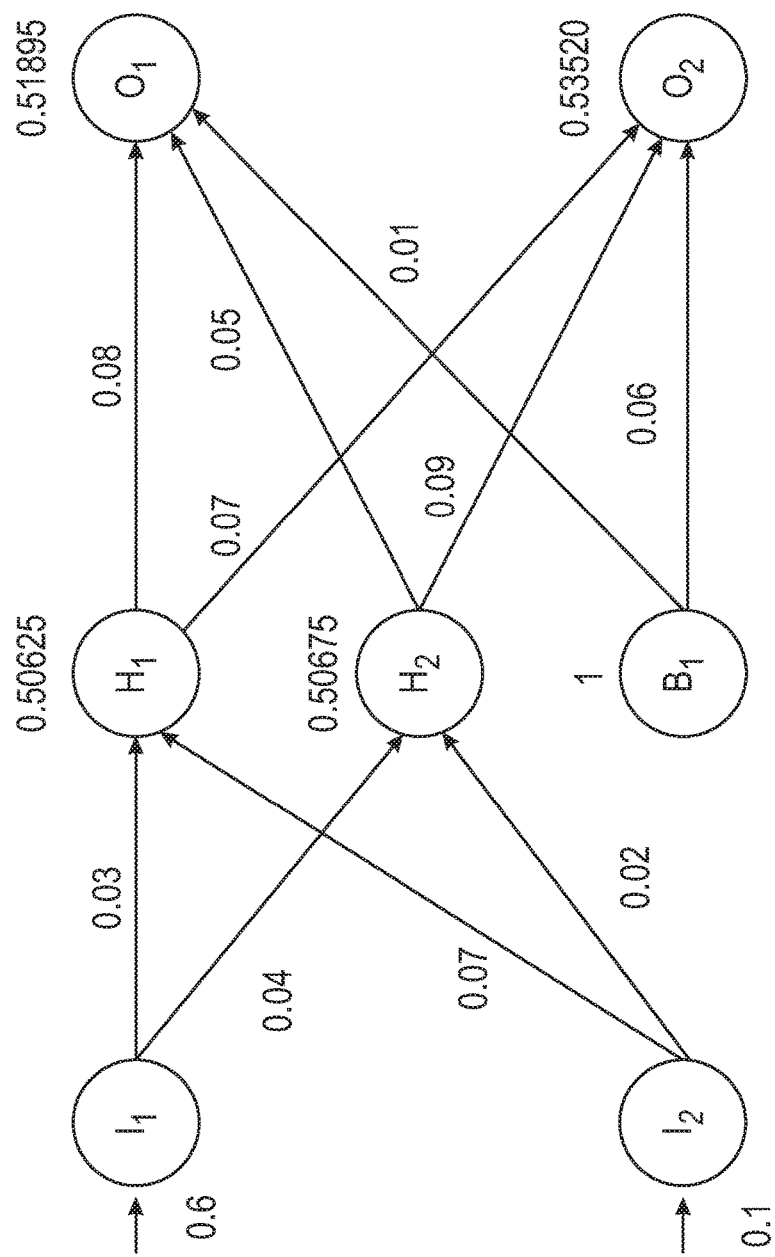
FIG. 25 is an illustration of exemplary computations of the NNM.

A NNM is a neural network architecture with a particular structure tailored to a particular problem statement. An exemplary problem statement the server's 2014 neural networks model is the prediction of whether a given patient from a particular facility is likely to suffer attempt a suicide. Using a trained NNM, the server 2014 predicts the likely outcome using a plurality of the properties or attributes of the patient (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 25 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self Organizing Map (Kohonen), among others. Feedback networks, for example Elman and Jordan Networks, are at times leveraged by the system particularly in instances where the sequence of events (order of data) is material. Each neural network model also has a defined activation function. In the exemplary neural network of FIG. 25, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 25). This calculation process is used during each model training iteration and subsequently when the trained model is used to make predictions from previously unseen input data:

```
H₁
Sum            = 0.6 * 0.03 + 0.1 * 0.07
               = 0.018 + 0.007
               = 0.025
Output = A(Sum) = 0.50625
H₂
Sum            = 0.6 * 0.04 + 0.1 * 0.02
               = 0.024 + 0.002
               = 0.027
Output = A(Sum) = 0.50675
O₁
Sum            = 0.50625 * 0.08 + 0.50675 * 0.05 + 1 * 0.01
               = 0.0405 + 0.0253375 + 0.01
               = 0.0758375
Output = A(Sum) = 0.51895
O₂
Sum            = 0.50625 * 0.07 + 0.50675 * 0.09 + 1 * 0.06
               = 0.0354375 + 0.0456075 + 0.06
               = 0.141045
Output = A(Sum) = 0.53520
```

During the training process, the synaptic weights are adjusted to minimize the error of the output. Thus, the final synaptic weights of the trained model are only known once model training is complete. After successful training of the model, the finalized synaptic weights are then used to make predictions.

Training the NNM

To train the NNM, the controller iteratively performs a machine learning algorithm (MLA) to adjust the values of the synaptic weights until a global error of an output of the NNM is below a predetermined acceptable global error. Performing of the MLA includes: generating an output value of the NNM for each past patient in the training data set using each patient's respective appointment events and related subsequent reached/not reached events (in follow up of the patient's no show for the respective appointment) as the input attributes; measuring the global error of the NNM based upon the output values of the NNM and the quantifiable outcomes of the past patients; and adjusting the values of the synaptic weights if the measured global error is not less than the predetermined acceptable global error to thereby obtain a trained NNM. Here, if the global error is never reached after number of outcomes, the model can be revised, such as number of hidden layers, neurons, etc.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\sum_n E^2}{n}$$

The mean square error (MSE) is the sum the square of all local errors divided by the total number of cases.

Sum of Square Errors (ESS)

$$\frac{\sum_n E^2}{2}$$

The sum of square errors (ESS) is the sum of the square of all local errors divided by two (2).

Root Mean Square Error (RMS)

$$\sqrt{\frac{\sum_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 26:
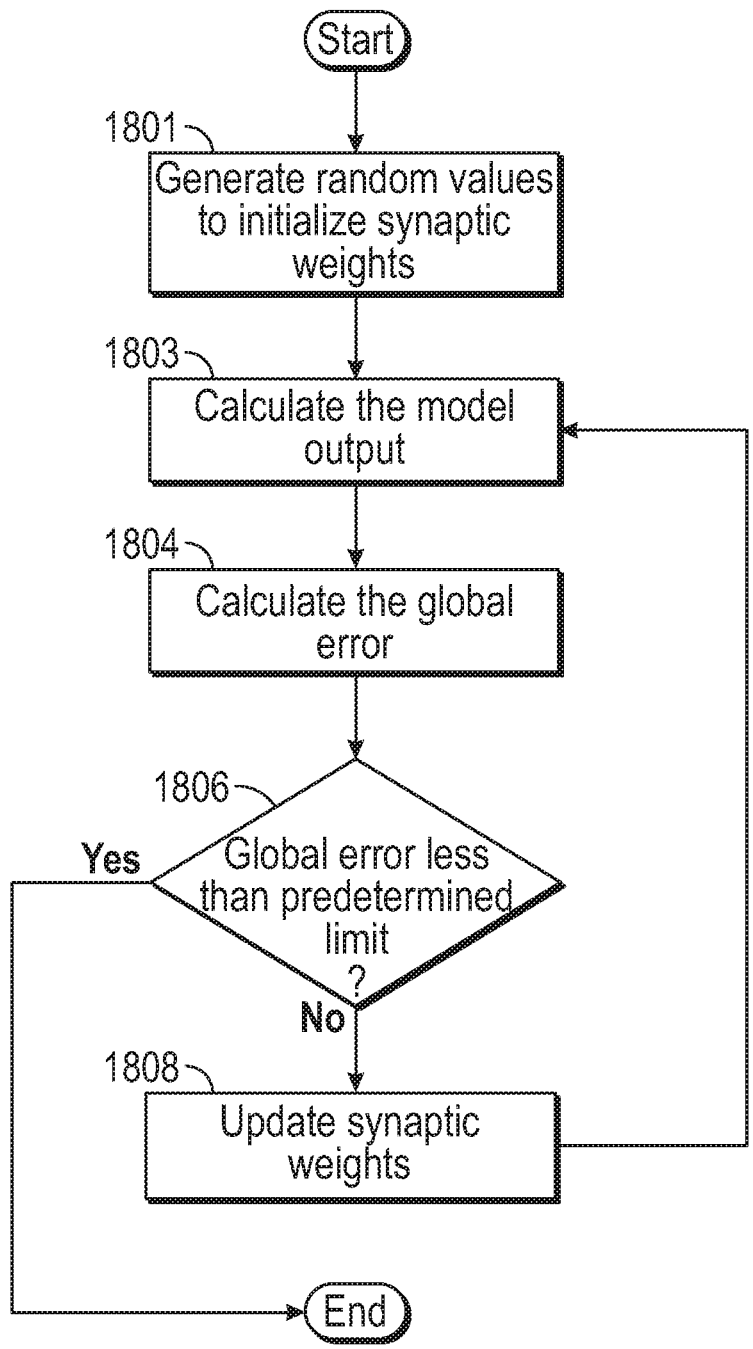
FIG. 26 is a flow diagram illustrating exemplary operations of the system for training the NNM.

Referring to FIG. 26, the approach for training the NNM based upon training data will be discussed. The training data is quantifiable outcomes (suicide attempt or no suicide attempt) of a plurality of past patient events and patient attributes of each of the past patient events. Initially, at 1801, values of the plurality of synaptic weights are assigned to random values. At 1803, the output values of the model are calculated for the current "row" or case in the training data being used for the current training iteration (i.e. "row" being the one event or case used for the current training iteration out of the available events in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another patient event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 27:
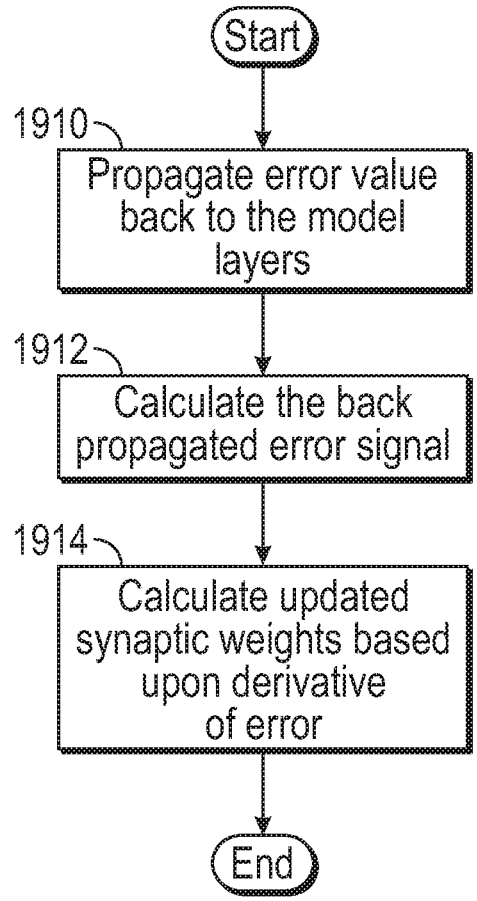
FIG. 27 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 27, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

To validate the NNM, the controller generates an output value of the trained NNM for each past patient appointment events of the validation data, wherein each of the output values represents a calculated quantifiable outcome of the respective patient risk for suicide; and determines if the output values correspond to the known quantifiable outcome within the predetermined global error; The creation and training of the NNM can be repeated until validation data results are satisfactory, defined as output data from the NNM being within the acceptable level of global error from the output values in the validation data set.

Figure 28:
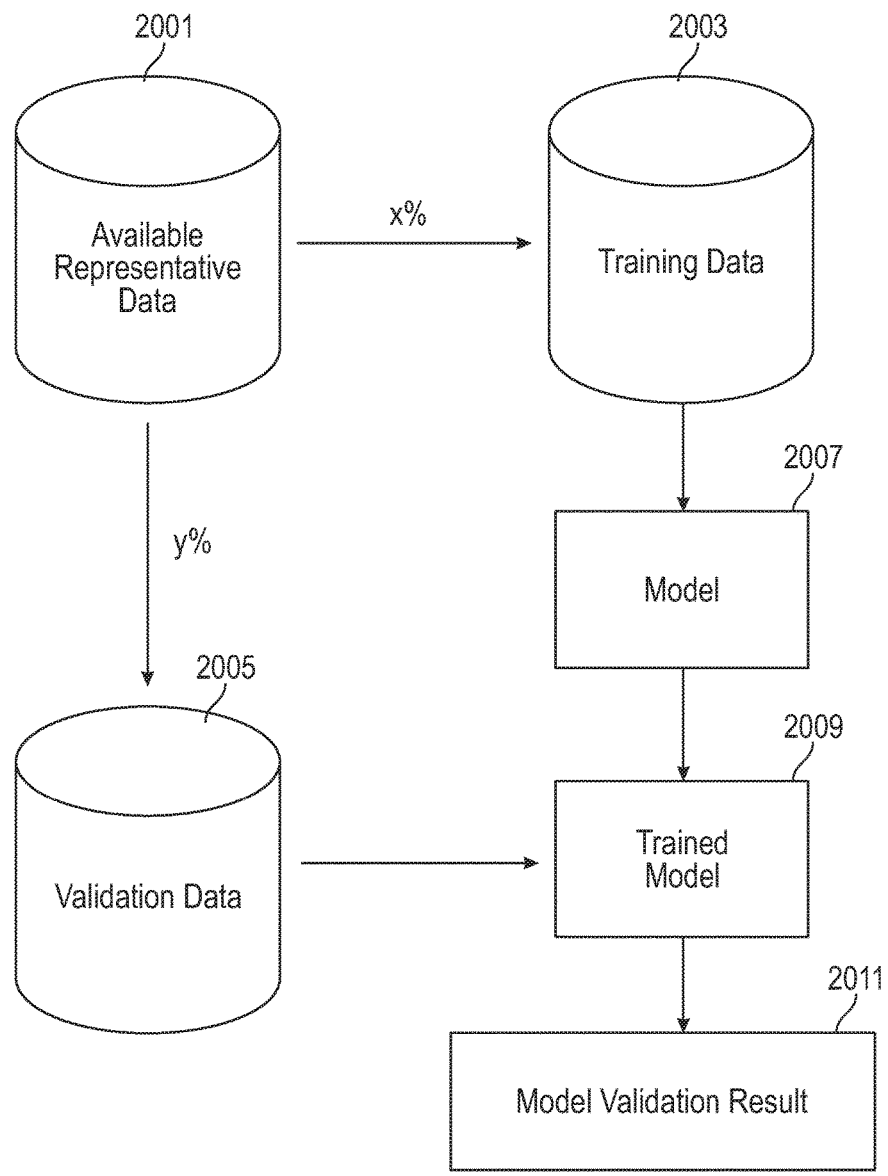
FIG. 28 is block diagram illustrating high level operations of the process for training the NNM and validating the trained NNM.

The training process for the NNM employs a representative data set, which can be a plurality of past patient events as discussed above. Referring to FIG. 28, the cases in the representative data set 2001 are divided into two unique data sets by some ratio or percent x allocated to the training data set 2003 and percent y allocated to the validation data set 2005. The ratio of cases allocated to the training data set 2003 versus those allocated to the validation data set 2005 varies. Before the allocation of cases to the training data set 2003 or the validation data set 2005, an optional step of data shuffling can be carried out by the system to help ensure all types of data in the representative data set 2001 gets distributed to both the training 2003 and the validation 2005 data sets. The training data set 2003 was used to train the NNM 2009 as discussed above. The validation data set 2005 can be used to validate the trained NNM 2009 because the real outcome of each case in the validation data set is known. The server can generate an output value (model validation result) 2011 of the trained NNM 2009 for each past patient event of the validation data set 2005, wherein each of the output values 2011 represents a calculated quantifiable outcome of the respective patient event. Then the server can determine if the output values 2011 correspond to the quantifiable outcome within the predetermined global error.

The training data set 2003 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2009 is then used to predict the outcome for cases in the validation data set 2005, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

The controller conducts pre-processing of input attributes of the new patient appointment and post no show follow up events (transactions). The input attributes can be, in this overly simplified example: seen at appointment (Boolean or yes/no) and outreached and successfully contacted after missed appointment (Boolean), as mentioned above. The controller generates an output value of the trained NNM based upon the input attributes of the new clinical patient transaction. The output value can be a predicted risk of suicide. Finally, the server device can compare the predicted risk for suicide with the threshold criteria or business logic the system has been configured with to determine whether notification or escalation is required.

The backend device receives a plurality of input attributes of a new patient event. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a suicide risk category (classification task) or a value such as the probability of a suicide attempt (regression task) to predict the outcome. For example, in the simplest case the de-normalized output value can be a Boolean value (suicide or no suicide). In another case, the output value can be a probability of a suicide occurring. In this case, the server may assign probability ranges which define particular suicide categories.

Unsupervised Learning

Figure 29:
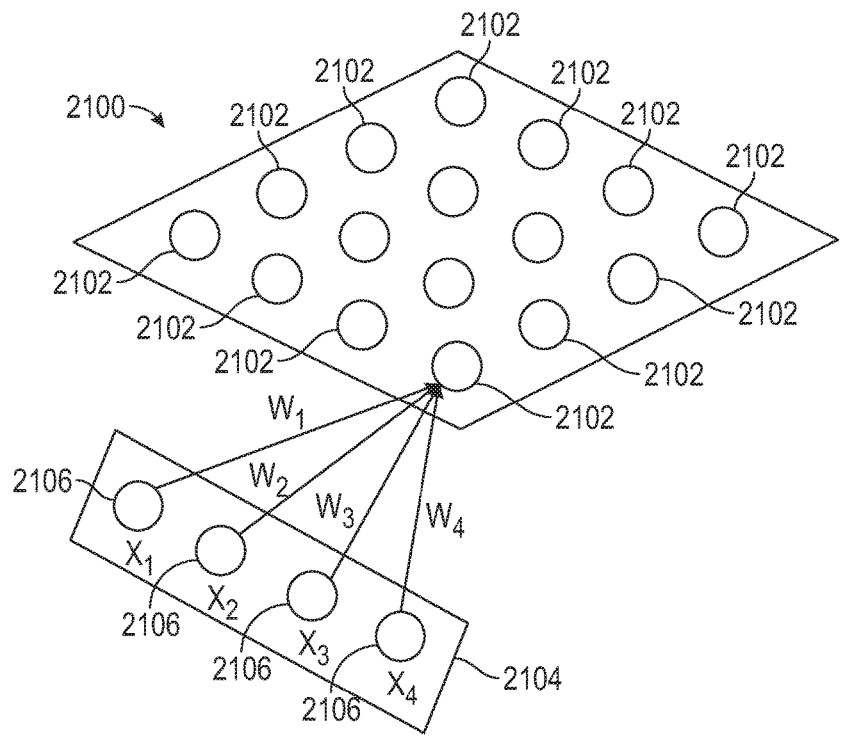
FIGS. 29-30 are illustrations of an exemplary Self-Organizing Map (SOM) and the input data set to the SOM network.
Figure 30:
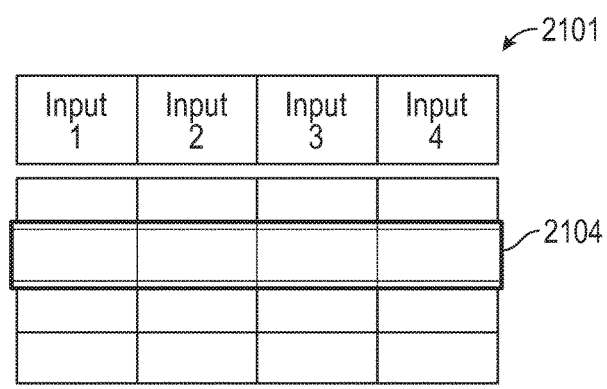
Figure 31:
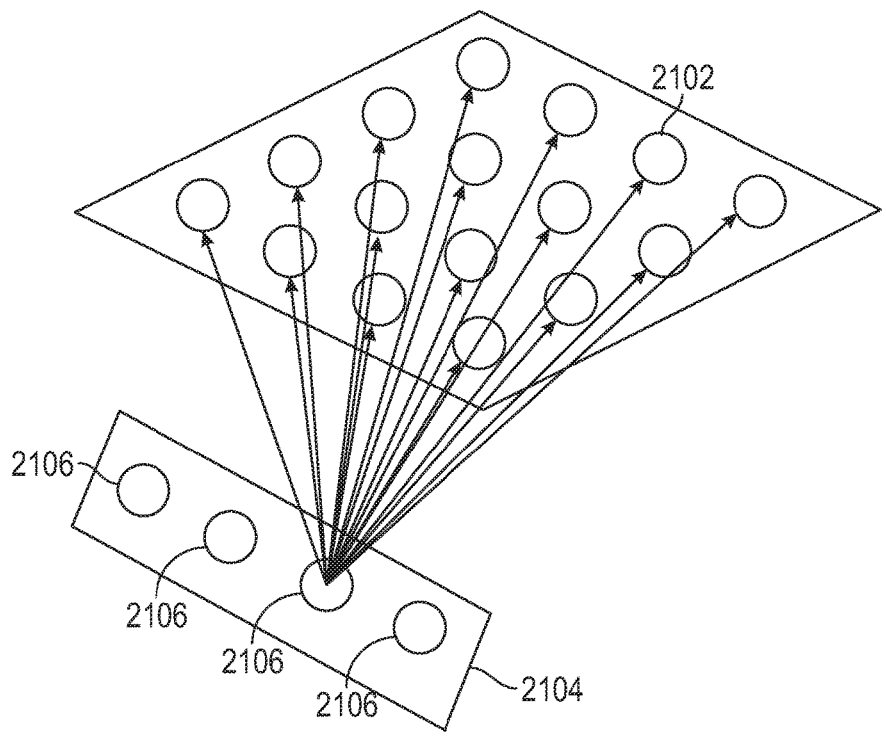
FIG. 31 is an illustration of how each node of the SOM network will contain the connection weights of the connections to all connected input nodes.
Figure 32:
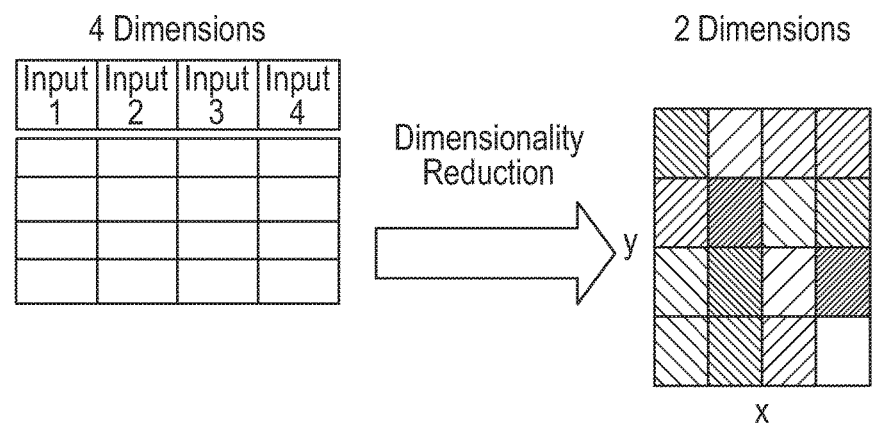
FIG. 32 is an illustration of the SOM network used to reduce dimensionality of the input data sets.

The server can also use unsupervised learning techniques as well as supervised learning techniques to determine the group or cluster to which particular patient events belong. Referring to FIGS. 29-31, a Self-Organizing Map (SOM)

2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 30). The specific number of inputs is dependent on the specifics of the data set. Each input node is connected to every node of the two (or three) dimensional SOM network (FIG. 31) and each connection has a synaptic connection weight (w), much like that in supervised networks. Each node 2102 of the SOM network 2100 will contain the connection weights of the connections to all connected input nodes. As partially shown in FIG. 31, each SOM network node 2102 is connected to all input nodes 2106, thus each node of the SOM network will have an equivalent number of connection weights (equivalent to the number of input nodes).

Figure 33:
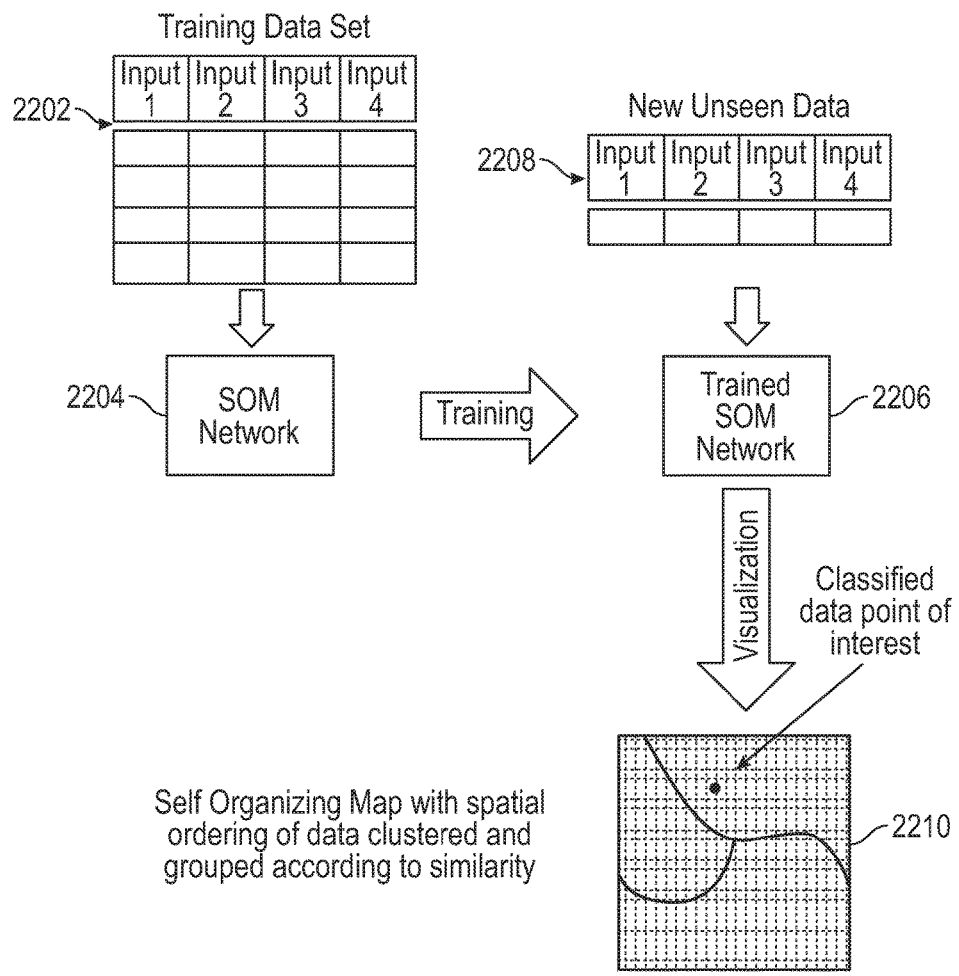
FIG. 33 is a block diagram illustrating high level operations of the process for training the SOM.

A representation of the process for creating, training and using the trained model is shown in FIG. 33. A training data set includes a plurality of patient attributes of past patient events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. As discussed later, the SOM image 2210 can be rendered on a client device.

Figure 34:
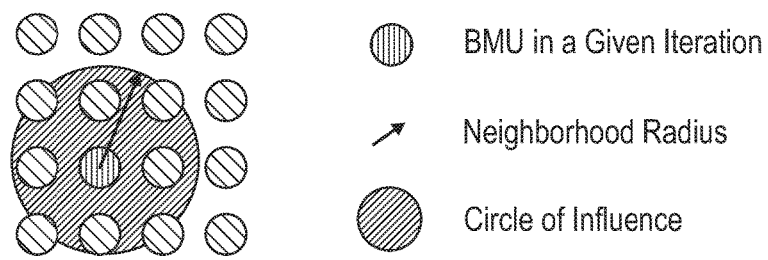
FIG. 34 is an illustration of the process for training the SOM network.

Referring to FIG. 34, the first step in SOM model training is to initialize values of the plurality of synaptic connection weights to random values. The next step is to randomly select one row (one past patient event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-(\frac{n}{\lambda})}$$

$r_0$=initial radius
n=iteration number
$\lambda$=time constant

Usually a large initial radius value is selected for the purpose of having the almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1) = W_k(n) + \alpha(n)h_{ck}(n)[x(n) - W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n) - W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Returning to FIG. 15, an exemplary data set includes a plurality of data [1, 2 . . . N], and a number of properties [1, 2 . . . N] for each data. The data set can be a plurality of past patient events and the properties can be a number of attributes of each past patient event. The high dimensionality of the data sets can make visualization of the data difficult. As illustrated in FIG. 33, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 35:
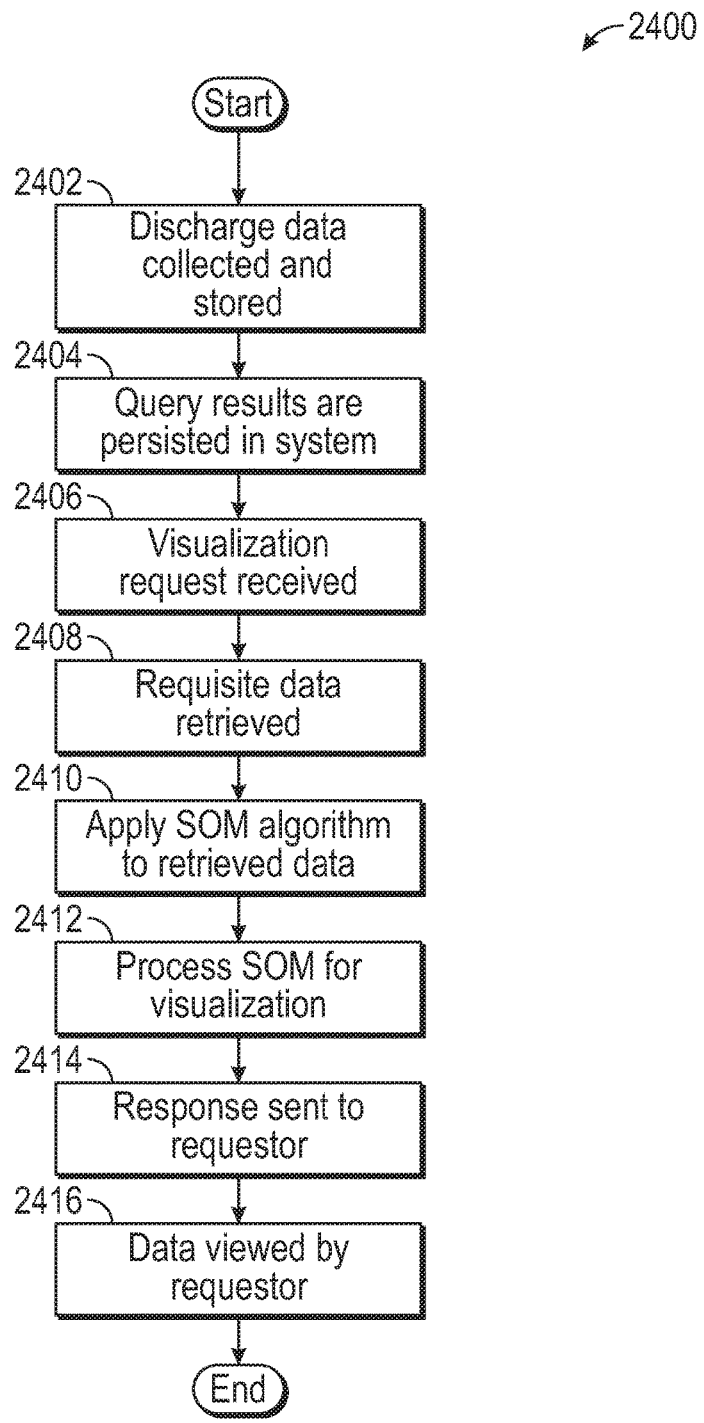
FIG. 35 is a flow diagram illustrating exemplary operations of the system to generate the graphical image including the visualization.

Referring to FIG. 35, an exemplary process 2400 by which the system can employ SOM network to take a data set of suicides defined by n-dimensional input attributes and generate a visualization of the results after passing the data into a SOM network will be discussed. At 2402, suicide data is collected and stored. For example, the DCE collects location data on the patient from the RFID tags as discussed above and transmits it to the backend devices. This data can be stored in the database at the server with respect to the patient as discussed above. At 2404, the server can maintain query results in the memory. At 2406, the server receives a visualization request from a client device or web browser via the network with query parameters. At 2408, the server sends a data request with the query parameters to the backend device, which retrieves from the database the data sets consistent with the request. At 2410, the backend device inputs the data sets to the trained SOM network. At 2412, the backend device generates a visualization or graphical image based upon the output from the SOM network. At 2414, the backend device sends the graphical image to the server, which either sends it to the client device and/or renders the image on a display of a website. The output produced can be groupings or clustering of discharges with similar characteristics, much like the classical "market segmentation" or "document classification" tasks for which SOMs are widely employed. This SOM output can be generated from a variety of vantage points or perspectives with one or more specified criteria, for example, specific occupations, or for only veterans, or only for a particular subset of patients processed by a particular employee, a group of employees, a service line, a group of service lines, a hospital facility or a group of hospital facilities in a given region, to name a few examples. SOM techniques can also be employed to predict the classification, type, or grouping of suicides leveraging the attributes or inputs from an already existing data set of suicides, for example.

Exemplary Implementation

Figure 36:
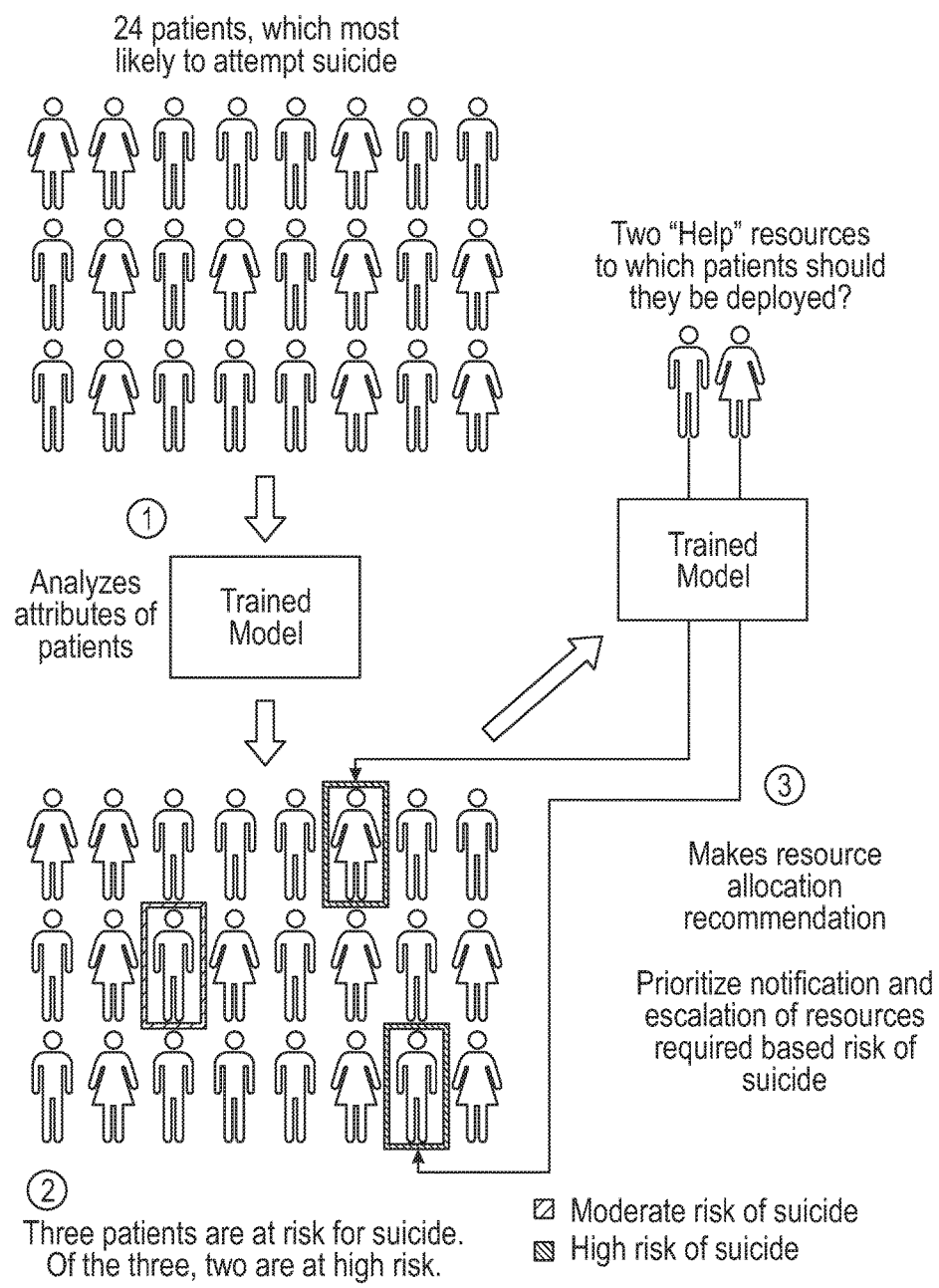
FIG. 36 is an illustration of an exemplary use case in which the trained model determines a suicide risk for a plurality of patient events and to which patient should help resources be deployed.

Referring to FIG. 36, an exemplary implementation will be discussed for a case in which a NNM is created, trained and validated to determine whether a given patient is likely to commit suicide. The backend devices (one or more server devices) use NNMs to predict which patients are at risk for suicide and to determine to which patients, if any, should more resources be allocated (i.e. the backend devices can determine whether there is an opportunity, or more specifically, a high probability, of successfully mitigating the likelihood of a given predicted suicide by allocating additional resource(s)).

In the example shown in FIG. 36, there are 24 patients that are being treated by a care group. The controller of the server may utilize a NNM that takes inputs as shown at 1, such as suicide risk category (moderate or significant risk for suicide) of the patient event, attributes of the patient, availability of lethal means, medication patient is using, attributes of available clinical resources (for example, the available help resources' expertise and past performance on suicides with similar patients or suicides with similar attributes), etc.

In doing so, the server can determine whether (the probability that) deployment of any given available resource(s) is likely to mitigate the predicted suicide risk for a given patient event; moreover, the server's NNMs can predict the probability of a suicide occurring that would potentially be reduced if a given resource allocation recommendation is made. As shown at 2, three patients are at risk for suicide with two being high risk and one being a moderate risk of suicide. Based on business logic and these results, the server may determine it does or does not recommend that any of the available additional resources be deployed as shown at 3. There are a number of approaches the server could take to arrive at a decision to recommend or not recommend the deployment of any available resource(s). One demonstrative approach the server might take would be to recommend the deployment of an available resource if the probability weighted reduction in the risk of suicide exceeded a particular threshold. If more than one potential allocation of available resources might be feasible at any given time, the business logic of the server, for example, could be configured such that the server issues the recommendation that in the net (summed together) results in the largest probability weighted suicide reduction for the hospital system as a whole at that moment—i.e. the constellation of recommendations at that moment that collectively has the maximum potential beneficial impact (probability weighted suicide reduction) for the hospital in question. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The resource allocation example herein is not intended to limit the scope of potential approaches to that described.

Therefore, the present disclosure concerns machine learning models, the disclosure's application of specific technical techniques that leverage the specific aspects or attributes of particular care episodes in hospital systems in conjunction with the other system components that permit the identification of the a suicide risk.

While only certain features of the invention have been illustrated and described herein, many modifications and changes will occur to those of ordinary skill in the art. The following claims are intended to cover all such modifications and changes.

What is claimed is:

1. A method for predicting a suicide risk associated with a new event, the method comprising:
   receiving a plurality of input attributes of the new event;
   performing pre-processing on the plurality of input attributes to generate an input data set;
   generating an output value from a trained model based upon the input data set; and
   classifying the output value into a suicide risk category.

2. The method of claim 1, wherein the plurality of input attributes are data associated with an electronic health record.

3. The method of claim 1, wherein the plurality of input attributes includes a pain scale rating value.

4. The method of claim 1, wherein the plurality of input attributes includes a substance abuse history value.

5. The method of claim 1, wherein the plurality of input attributes includes a suicide attempt history.

6. The method of claim 1, wherein the plurality of input attributes includes an anger rating value.

7. The method of claim 1, wherein the plurality of input attributes includes an inpatient psychiatric hospitalization history.

8. The method of claim 1, wherein the plurality of input attributes includes a prior diagnosis of one or more of depression, panic, anxiety and bipolar disorder.

9. The method of claim 1, wherein the plurality of input attributes includes a family loss history.

10. The method of claim 1, wherein the plurality of input attributes includes a rating of patients desire to continue to live or die.

11. The method of claim 1, further comprising:
storing a plurality of past events, each of the plurality of past events including a plurality of patient attributes and a quantifiable outcome; and
training a neural network model (NNM) to generate the trained model, wherein the training of the NNM includes:
performing pre-processing on the plurality of patient attributes for each of the plurality of past events to generate a plurality of input data sets;
dividing the plurality of past events into a first set of training data and a second set of validation data;
iteratively performing a machine learning algorithm (MLA) to update synaptic weights of the NNM based upon the training data; and
validating the NNM based upon the second set of validation data.

12. The method of claim 11, wherein the performing of the MLA includes measuring a global error in each training iteration for the NNM by:
calculating a local error, the local error being a difference between the output value of the NNM and the quantifiable outcome;
calculating the global error by summing all of the local errors in accordance with one of:
(1) Mean Square Error (MSE) formula $$\frac{\sum_{n} E^2}{n};$$

(2) Root Mean Square Error (RMS) formula $$\sqrt{\frac{\sum_{n} E^2}{n}};$$

and
(3) Sum of Square Errors (ESS) formula $$\frac{\sum_{n} E^2}{2},$$

wherein n represents a total number of the past events and E represents the local error.

13. The method of claim 1, wherein the trained model is a trained Self-Organizing Map (SOM) including a plurality of network nodes arranged in a grid or lattice and in fixed topological positions, an input layer with a plurality of input nodes representing the input attributes of the past events, wherein each of the plurality of input nodes is connected to all of the plurality of network nodes by a plurality of synaptic weights.

14. The method of claim 1, further comprising:
storing a plurality of past events, each of the plurality of past events including a plurality of patient attributes and a quantifiable outcome;
performing pre-processing on the plurality of patient attributes for each of the plurality of past events to generate a plurality of input data sets; and
training a SOM to generate the trained model, wherein the training of the SOM includes:
initializing values of the plurality of synaptic weights to random values, randomly selecting one past event and determining which of the plurality of network nodes is a best matching unit (BMU) according to a discriminant function, wherein the discriminant function is a Euclidean Distance; and
iteratively calculating a neighborhood radius associated with the BMU to determine neighboring network nodes for updating, and updating values of synoptic weights for neighboring network nodes within the calculated neighborhood radius for a fixed number of iterations to generate the trained model.

15. The method of claim 14, further comprising generating another SOM including the plurality of patient attributes to reduce dimensionality.

16. The method of claim 1, wherein the classifying the output value into the suicide risk category further includes classifying the output value into one of a high risk category, moderate risk category, low risk category and minimal risk category, wherein the suicide risk category based upon a risk of suicide with a following 72 hours.

\* \* \* \* \*